(12) United States Patent
Brenner et al.

(10) Patent No.: US 8,298,767 B2
(45) Date of Patent: Oct. 30, 2012

(54) COMPOSITIONS AND METHODS FOR INTRAMOLECULAR NUCLEIC ACID REARRANGEMENT

(75) Inventors: Sydney Brenner, Ely (GB); Gi Mikawa, Cambridge (GB); Robert Osborne, Great Chesterford (GB); Andrew Slatter, London (GB)

(73) Assignee: Population Genetics Technologies Ltd, Cambridge (GB)

( * ) Notice: Subject to any disclaimer, the term of this patent is extended or adjusted under 35 U.S.C. 154(b) by 0 days.

(21) Appl. No.: 13/387,343

(22) PCT Filed: Aug. 13, 2010

(86) PCT No.: PCT/IB2010/002243
§ 371 (c)(1),
(2), (4) Date: Feb. 15, 2012

(87) PCT Pub. No.: WO2011/021102
PCT Pub. Date: Feb. 24, 2011

(65) Prior Publication Data
US 2012/0135407 A1      May 31, 2012

Related U.S. Application Data

(60) Provisional application No. 61/288,792, filed on Dec. 21, 2009, provisional application No. 61/235,595, filed on Aug. 20, 2009.

(51) Int. Cl.
*C12Q 1/68* (2006.01)
*C12P 19/34* (2006.01)
*C07H 21/02* (2006.01)
*C07H 21/04* (2006.01)

(52) U.S. Cl. ...... 435/6.1; 435/6.11; 435/6.12; 435/91.2; 435/91.53; 435/287.2; 536/23.1; 536/24.2; 536/24.3; 536/24.33

(58) Field of Classification Search .......... 435/6.1, 435/6.11, 6.12, 91.2, 287.2; 536/23.1, 24.3, 536/24.33
See application file for complete search history.

(56) References Cited

U.S. PATENT DOCUMENTS

2007/0238113 A1  10/2007  Kanda et al.
2007/0259357 A1  11/2007  Brenner

FOREIGN PATENT DOCUMENTS

| EP | 1672064 A1 | 6/2006 |
| EP | 1841879 A2 | 10/2007 |
| WO | 2004/061083 A2 | 7/2004 |
| WO | 2007/018601 A1 | 2/2007 |

OTHER PUBLICATIONS

Laird et al, Hairpin-bisulfite PCR: Assessing epigenetic methylation patterns on complementary strands of individual DNA molecules, 2004, PNAS, 101, 204-209.*
Ushijima et al, Detection and interpretation of altered methylation patterns in cancer cells, 2005, Nature reviews, 5, 223-231.*
Imburgio et al, Studies of Promoter Recognition and Start Site Selection by T7 RNA Polymerase Using a Comprehensive Collection of Promoter Variants, 2000, Biochemistry, 39, 10419-10430.*
Yan, et al., "Rapid one-step construction of hairpin RNA", Biochemical and Biophysical Research Communications, 2009, 383:464-8.
PCT/IB2010/002243, International Search Report and Written Opinion, mailed Feb. 9, 2011, 13pgs.

* cited by examiner

*Primary Examiner* — Stephen Kapushoc
*Assistant Examiner* — Narayan Bhat
(74) *Attorney, Agent, or Firm* — Bozicevic, Field & Francis LLP; James S. Keddie

(57) ABSTRACT

Aspects of the present invention are drawn to processes for moving a region of interest in a polynucleotide from a first position to a second position with regard to a domain within the polynucleotide, also referred to as a "reflex method". In certain embodiments, the reflex method results in moving a region of interest into functional proximity to specific domain elements present in the polynucleotide (e.g., primer sites and/or MID). Compositions, kits and systems that find use in carrying out the reflex processes described herein are also provided.

18 Claims, 13 Drawing Sheets

A.

B.

Extension is best with Herculase, but 3'-5' exonuclease activity results in partial digestion of the desired 82 base product. Taq, which lacks 3'-5' exonuclease activity, shows a stronger band at the expected size of the final product.

A.

B.

Primer extension reactions with * may be performed such that isolation of single strand species is facilitated (e.g., using primers with binding moieties and/or multiple cycles of extension)

US 8,298,767 B2

COMPOSITIONS AND METHODS FOR INTRAMOLECULAR NUCLEIC ACID REARRANGEMENT

CROSS REFERENCE TO RELATED APPLICATIONS

This application is a filing under §371 of International Patent Application No. PCT/IB2010/002243, filed Aug. 13, 2010, which claims priority to U.S. Provisional Application No. 61/235,595, filed Aug. 20, 2009 and U.S. Provisional Application No. 61/288,792, filed Dec. 21, 2009; all of which are herein incorporated by reference.

BACKGROUND

We have previously described methods that enable tagging each of a population of fragmented genomes and then combining them together to create a 'population library' that can be processed and eventually sequenced as a mixture. The population tags enable analysis software to parse the sequence reads into files that can be attributed to a particular genome in the population. One limitation of the overall process stems from limitations of existing DNA sequencing technologies. In particular, if fragments in the regions of interest of the genome are longer than the lengths that can be sequenced by a particular technology, then such fragments will not be fully analyzed (since sequencing proceeds from an end of a fragment inward). Furthermore, a disadvantage of any sequencing technology dependent on fragmentation is that sequence changes in one part of a particular genomic region may not be able to be linked to sequence changes in other parts of the same genome (e.g., the same chromosome) because the sequence changes reside on different fragments. (See FIG. 5 and its description below).

The present invention removes the limitations imposed by current sequencing technologies as well as being useful in a number of other nucleic acid analyses.

SUMMARY OF THE INVENTION

Aspects of the present invention are drawn to processes for moving a region of interest in a polynucleotide from a first position to a second position with regard to a domain within the polynucleotide, also referred to as a "reflex method" (or reflex process, reflex sequence process, reflex reaction, and the like). In certain embodiments, the reflex method results in moving a region of interest into functional proximity to specific domain elements present in the polynucleotide (e.g., primer sites and/or MID). Compositions, kits and systems that find use in carrying out the reflex processes described herein are also provided.

BRIEF DESCRIPTION OF THE DRAWINGS

The invention is best understood from the following detailed description when read in conjunction with the accompanying drawings. It is emphasized that, according to common practice, the various features of the drawings are not to scale. Indeed, the dimensions of the various features are arbitrarily expanded or reduced for clarity. Included in the drawings are the following figures.

DEFINITIONS

Figure 1:
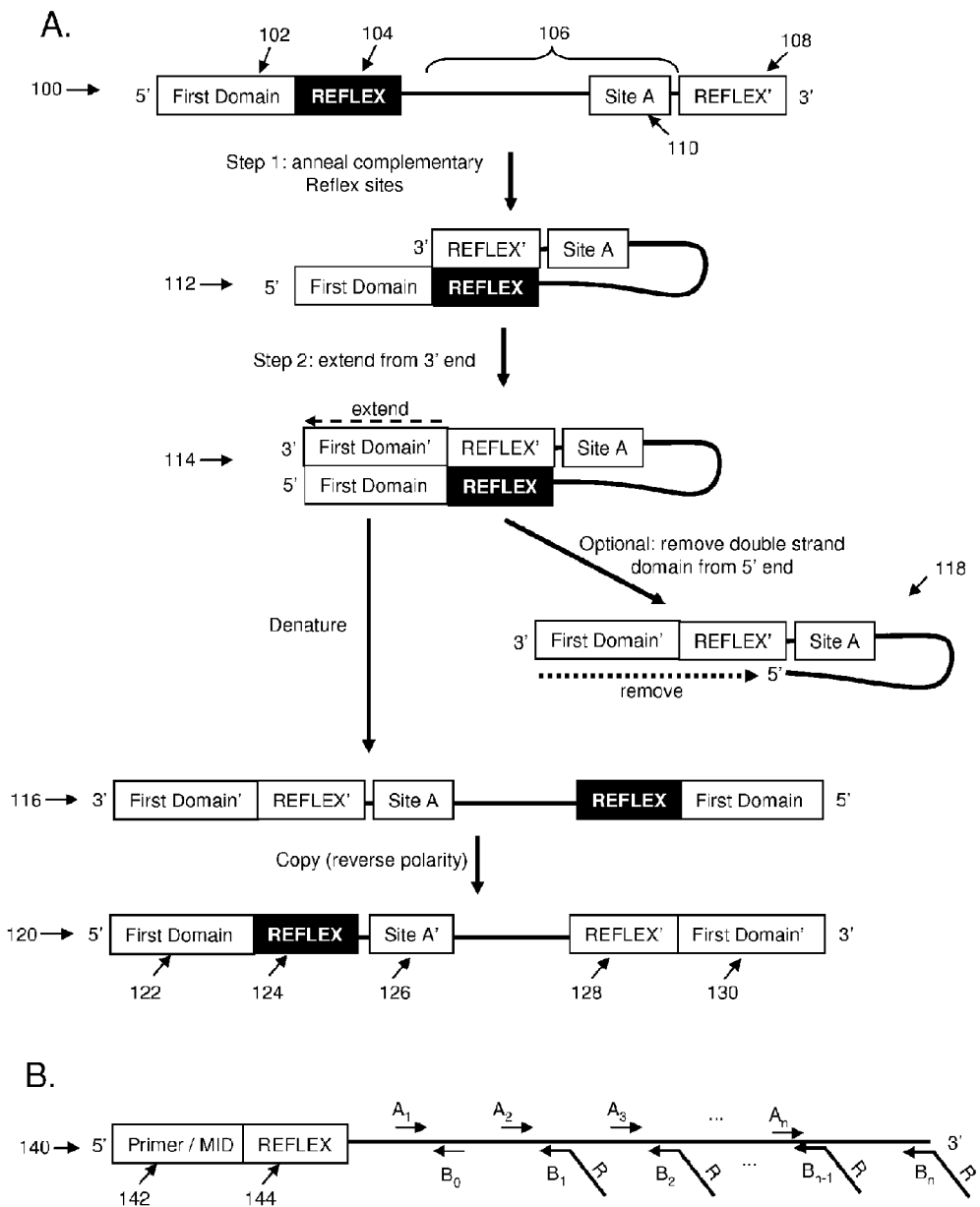
FIG. 1: Panel A is a schematic diagram illustrating moving a first domain from one site to another in a nucleic acid molecule using a reflex sequence. Panel B is a schematic diagram depicting the relative position of primer pairs ($A_n$-$B_n$ primers) that find use in aspects of the reflex process described herein.

Unless otherwise defined, all technical and scientific terms used herein have the same meaning as commonly understood by one of ordinary skill in the art to which this invention belongs. Still, certain elements are defined for the sake of clarity and ease of reference.

Terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like.

"Amplicon" means the product of a polynucleotide amplification reaction. That is, it is a population of polynucleotides, usually double stranded, that are replicated from one or more starting sequences. The one or more starting sequences may be one or more copies of the same sequence, or it may be a mixture of different sequences. Amplicons may be produced by a variety of amplification reactions whose products are multiple replicates of one or more target nucleic acids. Generally, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: Mullis et al, U.S. Pat. Nos. 4,683, 195; 4,965,188; 4,683,202; 4,800,159 (PCR); Gelfand et al, U.S. Pat. No. 5,210,015 (real-time PCR with "TAQMAN™" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g. "real-time PCR" described below, or "real-time NASBA" as described in Leone et al, Nucleic Acids Research, 26: 2150-2155 (1998), and like references. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salts, co-factors, scavengers, and the like.

The term "assessing" includes any form of measurement, and includes determining if an element is present or not. The terms "determining", "measuring", "evaluating", "assessing" and "assaying" are used interchangeably and includes quantitative and qualitative determinations. Assessing may be relative or absolute. "Assessing the presence of" includes determining the amount of something present, and/or determining whether it is present or absent. As used herein, the terms "determining," "measuring," and "assessing," and "assaying" are used interchangeably and include both quantitative and qualitative determinations.

Polynucleotides that are "asymmetrically tagged" have left and right adapter domains that are not identical. This process is referred to generically as attaching adapters asymmetrically or asymmetrically tagging a polynucleotide, e.g., a polynucleotide fragment. Production of polynucleotides having asymmetric adapter termini may be achieved in any convenient manner. Exemplary asymmetric adapters are described in: U.S. Pat. Nos. 5,712,126 and 6,372,434; U.S. Patent Publications 2007/0128624 and 2007/0172839; and PCT publication WO/2009/032167; all of which are incorporated by reference herein in their entirety. In certain embodiments, the asymmetric adapters employed are those described in U.S. patent application Ser. No. 12/432,080, filed on Apr. 29, 2009, incorporated herein by reference in its entirety.

As one example, a user of the subject invention may use an asymmetric adapter to tag polynucleotides. An "asymmetric adapter" is one that, when ligated to both ends of a double stranded nucleic acid fragment, will lead to the production of primer extension or amplification products that have non-identical sequences flanking the genomic insert of interest. The ligation is usually followed by subsequent processing steps so as to generate the non-identical terminal adapter sequences. For example, replication of an asymmetric adapter attached fragment(s) results in polynucleotide products in which there is at least one nucleic acid sequence difference, or nucleotide/nucleoside modification, between the terminal adapter sequences. Attaching adapters asymmetrically to polynucleotides (e.g., polynucleotide fragments) results in polynucleotides that have one or more adapter sequences on one end (e.g., one or more region or domain, e.g., a primer site) that are either not present or have a different nucleic acid sequence as compared to the adapter sequence on the other end. It is noted that an adapter that is termed an "asymmetric adapter" is not necessarily itself structurally asymmetric, nor does the mere act of attaching an asymmetric adapter to a polynucleotide fragment render it immediately asymmetric. Rather, an asymmetric adapter-attached polynucleotide, which has an identical asymmetric adapter at each end, produces replication products (or isolated single stranded polynucleotides) that are asymmetric with respect to the adapter sequences on opposite ends (e.g., after at least one round of amplification/primer extension).

Any convenient asymmetric adapter, or process for attaching adapters asymmetrically, may be employed in practicing the present invention. Exemplary asymmetric adapters are described in: U.S. Pat. Nos. 5,712,126 and 6,372,434; U.S. Patent Publications 2007/0128624 and 2007/0172839; and PCT publication WO/2009/032167; all of which are incorporated by reference herein in their entirety. In certain embodiments, the asymmetric adapters employed are those described in U.S. patent application Ser. No. 12/432,080, filed on Apr. 29, 2009, incorporated herein by reference in its entirety.

"Complementary" or "substantially complementary" refers to the hybridization or base pairing or the formation of a duplex between nucleotides or nucleic acids, such as, for instance, between the two strands of a double stranded DNA molecule or between an oligonucleotide primer and a primer site on a single stranded nucleic acid. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

"Duplex" means at least two oligonucleotides and/or polynucleotides that are fully or partially complementary undergo Watson-Crick type base pairing among all or most of their nucleotides so that a stable complex is formed. The terms "annealing" and "hybridization" are used interchangeably to mean the formation of a stable duplex. "Perfectly matched" in reference to a duplex means that the poly- or oligonucleotide strands making up the duplex form a double stranded structure with one another such that every nucleotide in each strand undergoes Watson-Crick base pairing with a nucleotide in the other strand. A stable duplex can include Watson-Crick base pairing and/or non-Watson-Crick base pairing between the strands of the duplex (where base pairing means the forming hydrogen bonds). In certain embodiments, a non-Watson-Crick base pair includes a nucleoside analog, such as deoxyinosine, 2,6-diaminopurine, PNAs, LNA's and the like. In certain embodiments, a non-Watson-Crick base pair includes a "wobble base", such as deoxyinosine, 8-oxo-dA, 8-oxo-dG and the like, where by "wobble base" is meant a nucleic acid base that can base pair with a first nucleotide base in a complementary nucleic acid strand but that, when employed as a template strand for nucleic acid synthesis, leads to the incorporation of a second, different nucleotide base into the synthesizing strand (wobble bases are described in further detail below). A "mismatch" in a duplex between two oligonucleotides or polynucleotides means that a pair of nucleotides in the duplex fails to undergo Watson-Crick bonding.

"Genetic locus," "locus," or "locus of interest" in reference to a genome or target polynucleotide, means a contiguous sub-region or segment of the genome or target polynucleotide. As used herein, genetic locus, locus, or locus of interest may refer to the position of a nucleotide, a gene or a portion of a gene in a genome, including mitochondrial DNA or other non-chromosomal DNA (e.g., bacterial plasmid), or it may refer to any contiguous portion of genomic sequence whether or not it is within, or associated with, a gene. A genetic locus, locus, or locus of interest can be from a single nucleotide to a segment of a few hundred or a few thousand nucleotides in length or more. In general, a locus of interest will have a reference sequence associated with it (see description of "reference sequence" below).

"Kit" refers to any delivery system for delivering materials or reagents for carrying out a method of the invention. In the context of reaction assays, such delivery systems include systems that allow for the storage, transport, or delivery of reaction reagents (e.g., probes, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains probes.

"Ligation" means to form a covalent bond or linkage between the termini of two or more nucleic acids, e.g. oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon of a terminal nucleotide of one oligonucleotide with 3' carbon of another oligonucleotide. A variety of template-driven ligation reactions are described in the following references, which are incorporated by reference: Whiteley et al, U.S. Pat. No. 4,883,750; Letsinger et al, U.S. Pat. No. 5,476,930; Fung et al, U.S. Pat. No. 5,593,826; Kool, U.S. Pat. No. 5,426,180; Landegren et al, U.S. Pat. No. 5,871,921; Xu and Kool, Nucleic Acids Research, 27: 875-881 (1999); Higgins et al, Methods in Enzymology, 68: 50-71 (1979); Engler et al, The Enzymes, 15: 3-29 (1982); and Namsaraev, U.S. patent publication 2004/0110213.

"Multiplex Identifier" (MID) as used herein refers to a tag or combination of tags associated with a polynucleotide whose identity (e.g., the tag DNA sequence) can be used to differentiate polynucleotides in a sample. In certain embodiments, the MID on a polynucleotide is used to identify the source from which the polynucleotide is derived. For example, a nucleic acid sample may be a pool of polynucleotides derived from different sources, (e.g., polynucleotides derived from different individuals, different tissues or cells, or polynucleotides isolated at different times points), where the polynucleotides from each different source are tagged with a unique MID. As such, a MID provides a correlation between a polynucleotide and its source. In certain embodiments, MIDs are employed to uniquely tag each individual polynucleotide in a sample. Identification of the number of unique MIDs in a sample can provide a readout of how many individual polynucleotides are present in the sample (or from how many original polynucleotides a manipulated polynucleotide sample was derived; see, e.g., U.S. Pat. No. 7,537,897, issued on May 26, 2009, incorporated herein by reference in its entirety). MIDs can range in length from 2 to 100 nucleotide bases or more and may include multiple subunits, where each different MID has a distinct identity and/or order of subunits. Exemplary nucleic acid tags that find use as MIDs are described in U.S. Pat. No. 7,544,473, issued on Jun. 6, 2009, and titled "Nucleic Acid Analysis Using Sequence Tokens", as well as U.S. Pat. No. 7,393,665, issued on Jul. 1, 2008, and titled "Methods and Compositions for Tagging and Identifying Polynucleotides", both of which are incorporated herein by reference in their entirety for their description of nucleic acid tags and their use in identifying polynucleotides. In certain embodiments, a set of MIDs employed to tag a plurality of samples need not have any particular common property (e.g., Tm, length, base composition, etc.), as the methods described herein can accommodate a wide variety of unique MID sets. It is emphasized here that MIDs need only be unique within a given experiment. Thus, the same MID may be used to tag a different sample being processed in a different experiment. In addition, in certain experiments, a user may use the same MID to tag a subset of different samples within the same experiment. For example, all samples derived from individuals having a specific phenotype may be tagged with the same MID, e.g., all samples derived from control (or wildtype) subjects can be tagged with a first MID while subjects having a disease condition can be tagged with a second MID (different than the first MID). As another example, it may be desirable to tag different samples derived from the same source with different MIDs (e.g., samples derived over time or derived from different sites within a tissue). Further, MIDs can be generated in a variety of different ways, e.g., by a combinatorial tagging approach in which one MID is attached by ligation and a second MID is attached by primer extension. Thus, MIDs can be designed and implemented in a variety of different ways to track polynucleotide fragments during processing and analysis, and thus no limitation in this regard is intended.

"Nucleoside" as used herein includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90: 543-584 (1990), or the like, with the proviso that they are capable of specific hybridization. Such analogs include synthetic nucleosides designed to enhance binding properties, reduce complexity, increase specificity, and the like. Polynucleotides comprising analogs with enhanced hybridization or nuclease resistance properties are described in Uhlman and Peyman (cited above); Crooke et al, Exp. Opin. Ther. Patents, 6: 855-870 (1996); Mesmaeker et al, Current Opinion in Structual Biology, 5: 343-355 (1995); and the like. Exemplary types of polynucleotides that are capable of enhancing duplex stability include oligonucleotide N3'→P5' phosphoramidates (referred to herein as "amidates"), peptide nucleic acids (referred to herein as "PNAs"), oligo-2'-O-alkylribonucleotides, polynucleotides containing C-5 propynylpyrimidines, locked nucleic acids ("LNAs"), and like compounds. Such oligonucleotides are either available commercially or may be synthesized using methods described in the literature.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer sites, such reaction comprising one or more repetitions of the following steps: (i) denaturing the target nucleic acid, (ii) annealing primers to the primer sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature>90° C., primers annealed at a temperature in the range 50-75° C., and primers extended at a temperature in the range 72-78° C. The term "PCR" encompasses derivative forms of the reaction, including but not limited to, RT-PCR, real-time PCR, nested PCR, quantitative PCR, multiplexed PCR, and the like. Reaction volumes range from a few hundred nanoliters, e.g. 200 nL, to a few hundred μL, e.g. 200 μL. "Reverse transcription PCR," or "RT-PCR," means a PCR that is preceded by a reverse transcription reaction that converts a target RNA to a complementary single stranded DNA, which is then amplified, e.g. Tecott et al, U.S. Pat. No. 5,168,038, which patent is incorporated herein by reference. "Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al, U.S. Pat. No. 5,210,015 ("TAQ-MAN™"); Wittwer et al, U.S. Pat. Nos. 6,174,670 and 6,569,627 (intercalating dyes); Tyagi et al, U.S. Pat. No. 5,925,517 (molecular beacons); which patents are incorporated herein by reference. Detection chemistries for real-time PCR are reviewed in Mackay et al, Nucleic Acids Research, 30: 1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al, Anal. Biochem., 273: 221-228 (1999)(two-color real-time PCR). Usually, distinct sets of primers are employed for each sequence being amplified.

"Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin, GAPDH, $\beta_2$-microglobulin, ribosomal RNA, and the like. Techniques for quantitative PCR are well-known to those of ordinary skill in the art, as exemplified in the following references that are incorporated by reference: Freeman et al, Biotechniques, 26: 112-126 (1999); Becker-Andre et al, Nucleic Acids Research, 17: 9437-9447 (1989); Zimmerman et al, Biotechniques, 21: 268-279 (1996); Diviacco et al, Gene, 122: 3013-3020 (1992); Becker-Andre et al, Nucleic Acids Research, 17: 9437-9446 (1989); and the like.

"Polynucleotide" or "oligonucleotide" is used interchangeably and each means a linear polymer of nucleotide monomers. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, wobble base pairing, or the like. As described in detail below, by "wobble base" is meant a nucleic acid base that can base pair with a first nucleotide base in a complementary nucleic acid strand but that, when employed as a template strand for nucleic acid synthesis, leads to the incorporation of a second, different nucleotide base into the synthesizing strand. Such monomers and their internucleosidic linkages may be naturally occurring or may be analogs thereof, e.g. naturally occurring or non-naturally occurring analogs. Non-naturally occurring analogs may include peptide nucleic acids (PNAs, e.g., as described in U.S. Pat. No. 5,539,082, incorporated herein by reference), locked nucleic acids (LNAs, e.g., as described in U.S. Pat. No. 6,670,461, incorporated herein by reference), phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moieties, or bases at any or some positions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references.

"Primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Usually primers are extended by a DNA polymerase. Primers are generally of a length compatible with their use in synthesis of primer extension products, and are usually are in the range of between 8 to 100 nucleotides in length, such as 10 to 75, 15 to 60, 15 to 40, 18 to 30, 20 to 40, 21 to 50, 22 to 45, 25 to 40, and so on, more typically in the range of between 18-40, 20-35, 21-30 nucleotides long, and any length between the stated ranges. Typical primers can be in the range of between 10-50 nucleotides long, such as 15-45, 18-40, 20-30, 21-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length.

Primers are usually single-stranded for maximum efficiency in amplification, but may alternatively be double-stranded. If double-stranded, the primer is usually first treated to separate its strands before being used to prepare extension products. This denaturation step is typically affected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

A "primer pair" as used herein refers to first and second primers having nucleic acid sequence suitable for nucleic acid-based amplification of a target nucleic acid. Such primer pairs generally include a first primer having a sequence that is the same or similar to that of a first portion of a target nucleic acid, and a second primer having a sequence that is complementary to a second portion of a target nucleic acid to provide for amplification of the target nucleic acid or a fragment thereof. Reference to "first" and "second" primers herein is arbitrary, unless specifically indicated otherwise. For example, the first primer can be designed as a "forward primer" (which initiates nucleic acid synthesis from a 5' end of the target nucleic acid) or as a "reverse primer" (which initiates nucleic acid synthesis from a 5' end of the extension product produced from synthesis initiated from the forward primer). Likewise, the second primer can be designed as a forward primer or a reverse primer.

"Primer site" (e.g., a sequencing primer site, and amplification primer site, etc.) as used herein refers to a domain in a polynucleotide that includes the sequence of a primer (e.g., a sequencing primer) and/or the complementary sequence of a primer. When present in single stranded form (e.g., in a single stranded polynucleotide), a primer site can be either the identical sequence of a primer or the complementary sequence of a primer. When present in double stranded form, a primer site contains the sequence of a primer hybridized to the complementary sequence of the primer. Thus, a primer site is a region of a polynucleotide that is either identical to or complementary to the sequence of a primer (when in a single stranded form) or a double stranded region formed between a primer sequence and its complement. Primer sites may be present in an adapter attached to a polynucleotide. The specific orientation of a primer site can be inferred by those of ordinary skill in the art from the structural features of the relevant polynucleotide and/or context in which it is used.

"Readout" means a parameter, or parameters, which are measured and/or detected that can be converted to a number or value. In some contexts, readout may refer to an actual numerical representation of such collected or recorded data. For example, a readout of fluorescent intensity signals from a microarray is the address and fluorescence intensity of a signal being generated at each hybridization site of the microarray; thus, such a readout may be registered or stored in various ways, for example, as an image of the microarray, as a table of numbers, or the like.

"Reflex site", "reflex sequence" and equivalents are used to indicate sequences in a polynucleotide that are employed to move a domain intramolecularly from its initial location to a different location in the polynucleotide. The sequence of a reflex site can be added to a polynucleotide of interest (e.g., present in an adapter ligated to the polynucleotide), be based on a sequence naturally present within the polynucleotide of interest (e.g., a genomic sequence in the polynucleotide), or a combination of both. The reflex sequence is chosen so as to be distinct from other sequences in the polynucleotide (i.e., with little sequence homology to other sequences likely to be present in the polynucleotide, e.g., genomic or sub-genomic sequences to be processed). As such, a reflex sequence should be selected so as to not hybridize to any sequence except its complement under the conditions employed in the reflex processes herein described. As described later in this application, the complement to the reflex sequence is inserted on the same strand of the polynucleotide (e.g., the same strand of a double-stranded polynucleotide or on the same single stranded polynucleotide) in a particular location so as to facilitate an intramolecular binding event on such particular strand. Reflex sequences employed in the reflex process described herein can thus have a wide range of lengths and sequences. Reflex sequences may range from 5 to 200 nucleotide bases in length.

"Solid support", "support", and "solid phase support" are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. Microarrays usually comprise at least one planar solid phase support, such as a glass microscope slide.

"Specific" or "specificity" in reference to the binding of one molecule to another molecule, such as a labeled target sequence for a probe, means the recognition, contact, and formation of a stable complex between the two molecules, together with substantially less recognition, contact, or complex formation of that molecule with other molecules. In one aspect, "specific" in reference to the binding of a first molecule to a second molecule means that to the extent the first molecule recognizes and forms a complex with another molecule in a reaction or sample, it forms the largest number of the complexes with the second molecule. Preferably, this largest number is at least fifty percent. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, biotin-avidin or biotin-streptavidin interactions, receptor-ligand interactions, and the like. As used herein, "contact" in reference to specificity or specific binding means two molecules are close enough that weak noncovalent chemical interactions, such as Van der Waal forces, hydrogen bonding, base-stacking interactions, ionic and hydrophobic interactions, and the like, dominate the interaction of the molecules.

As used herein, the term "$T_m$" is used in reference to the "melting temperature." The melting temperature is the temperature (e.g., as measured in ° C.) at which a population of double-stranded nucleic acid molecules becomes half dissociated into single strands. Several equations for calculating the $T_m$ of nucleic acids are known in the art (see e.g., Anderson and Young, Quantitative Filter Hybridization, in Nucleic Acid Hybridization (1985). Other references (e.g., Allawi, H. T. & SantaLucia, J., Jr., Biochemistry 36, 10581-94 (1997)) include alternative methods of computation which take structural and environmental, as well as sequence characteristics into account for the calculation of $T_m$.

"Sample" means a quantity of material from a biological, environmental, medical, or patient source in which detection, measurement, or labeling of target nucleic acids is sought. On the one hand it is meant to include a specimen or culture (e.g., microbiological cultures). On the other hand, it is meant to include both biological and environmental samples. A sample may include a specimen of synthetic origin. Biological samples may be animal, including human, fluid, solid (e.g., stool) or tissue, as well as liquid and solid food and feed products and ingredients such as dairy items, vegetables, meat and meat by-products, and waste. Biological samples may include materials taken from a patient including, but not limited to cultures, blood, saliva, cerebral spinal fluid, pleural fluid, milk, lymph, sputum, semen, needle aspirates, and the like. Biological samples may be obtained from all of the various families of domestic animals, as well as feral or wild animals, including, but not limited to, such animals as ungulates, bear, fish, rodents, etc. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

The terms "upstream" and "downstream" in describing nucleic acid molecule orientation and/or polymerization are used herein as understood by one of skill in the art. As such, "downstream" generally means proceeding in the 5' to 3' direction, i.e., the direction in which a nucleotide polymerase normally extends a sequence, and "upstream" generally means the converse. For example, a first primer that hybridizes "upstream" of a second primer on the same target nucleic acid molecule is located on the 5' side of the second primer (and thus nucleic acid polymerization from the first primer proceeds towards the second primer).

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

DETAILED DESCRIPTION OF THE INVENTION

The invention is drawn to compositions and methods for intramolecular nucleic acid rearrangement that find use in various applications of genetic analysis, including sequencing, as well as general molecular biological manipulations of polynucleotide structures.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a nucleic acid" includes a plurality of such nucleic acids and reference to "the compound" includes reference to one or more compounds and equivalents thereof known to those skilled in the art, and so forth.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual*, and *Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), Lehninger, A., *Principles of Biochemistry* $3^{rd}$ Ed., W.H. Freeman Pub., New York, N.Y. and Berg et al. (2002) *Biochemistry, $5^{th}$* Ed., W.H. Freeman Pub., New York, N.Y., all of which are herein incorporated in their entirety by reference for all purposes.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As summarized above, aspects of the present invention are drawn to the use of a 'reflex' sequence present in a polynucleotide (e.g., in an adapter structure of the polynucleotide, in a genomic region of the polynucleotide, or a combination of both) to move a domain of the polynucleotide intra-molecularly from a first location to a second location. The reflex process described herein finds use in any number of applications, e.g., placing functional elements of a polynucleotide (e.g., sequencing primer sites and/or MID tags) into proximity to a desired sub-region of interest.

Nucleic Acids

The reflex process (as described in detail below) can be employed for the manipulation and analysis of nucleic acid sequences of interest from virtually any nucleic acid source, including but not limited to genomic DNA, complementary DNA (cDNA), RNA (e.g., messenger RNA, ribosomal RNA, short interfering RNA, microRNA, etc.), plasmid DNA, mitochondrial DNA, synthetic DNA, etc. Furthermore, any organism, organic material or nucleic acid-containing substance can be used as a source of nucleic acids to be processed in accordance with the present invention including, but not limited to, plants, animals (e.g., reptiles, mammals, insects, worms, fish, etc.), tissue samples, bacteria, fungi (e.g., yeast), phage, viruses, cadaveric tissue, archaeological/ancient samples, etc. In certain embodiments, the nucleic acids in the nucleic acid sample are derived from a mammal, where in certain embodiments the mammal is a human.

In certain embodiments, the nucleic acid sequences are enriched prior to the reflex sequence process. By enriched is meant that the nucleic acid is subjected to a process that reduces the complexity of the nucleic acids, generally by increasing the relative concentration of particular nucleic acid species in the sample (e.g., having a specific locus of interest, including a specific nucleic acid sequence, lacking a locus or sequence, being within a specific size range, etc.). There are a wide variety of ways to enrich nucleic acids having a specific characteristic(s) or sequence, and as such any convenient method to accomplish this may be employed. The enrichment (or complexity reduction) can take place at any of a number of steps in the process, and will be determined by the desires of the user. For example, enrichment can take place in individual parental samples (e.g., untagged nucleic acids prior to adaptor ligation) or in multiplexed samples (e.g., nucleic acids tagged with primer sites, MID and/or reflex sequences and pooled; MID are described in further detail below).

In certain embodiments, nucleic acids in the nucleic acid sample are amplified prior to analysis. In certain of these embodiments, the amplification reaction also serves to enrich a starting nucleic acid sample for a sequence or locus of interest. For example, a starting nucleic acid sample can be subjected to a polymerase chain reaction (PCR) that amplifies one or more region of interest. In certain embodiments, the amplification reaction is an exponential amplification reaction, whereas in certain other embodiments, the amplification reaction is a linear amplification reaction. Any convenient method for performing amplification reactions on a starting nucleic acid sample can be used in practicing the subject invention. In certain embodiments, the nucleic acid polymerase employed in the amplification reaction is a polymerase that has proofreading capability (e.g., phi29 DNA Polymerase, *Thermococcus litoralis* DNA polymerase, *Pyrococcus furiosus* DNA polymerase, etc.).

In certain embodiments, the nucleic acid sample being analyzed is derived from a single source (e.g., a single organism, virus, tissue, cell, subject, etc.), whereas in other embodiments, the nucleic acid sample is a pool of nucleic acids extracted from a plurality of sources (e.g., a pool of nucleic acids from a plurality of organisms, tissues, cells, subjects, etc.), where by "plurality" is meant two or more. As such, in certain embodiments, a nucleic acid sample can contain nucleic acids from 2 or more sources, 3 or more sources, 5 or more sources, 10 or more sources, 50 or more sources, 100 or more sources, 500 or more sources, 1000 or more sources, 5000 or more sources, up to and including about 10,000 or more sources.

In certain embodiments, nucleic acid fragments that are to be pooled with nucleic acid fragments derived from a plurality of sources (e.g., a plurality of organisms, tissues, cells, subjects, etc.), where by "plurality" is meant two or more. In such embodiments, the nucleic acids derived from each source includes a multiplex identifier (MID) such that the source from which the each tagged nucleic acid fragment was derived can be determined. In such embodiments, each nucleic acid sample source is correlated with a unique MID, where by unique MID is meant that each different MID employed can be differentiated from every other MID employed by virtue of at least one characteristic, e.g., the nucleic acid sequence of the MID. Any type of MID can be used, including but not limited to those described in co-pending U.S. patent application Ser. No. 11/656,746, filed on Jan. 22, 2007, and titled "Nucleic Acid Analysis Using Sequence Tokens", as well as U.S. Pat. No. 7,393,665, issued on Jul. 1, 2008, and titled "Methods and Compositions for Tagging and Identifying Polynucleotides", both of which are incorporated herein by reference in their entirety for their description of nucleic acid tags and their use in identifying polynucleotides. In certain embodiments, a set of MIDs employed to tag a plurality of samples need not have any particular common property (e.g., $T_m$, length, base composition, etc.), as the asymmetric tagging methods (and many tag readout methods, including but not limited to sequencing of the tag or measuring the length of the tag) can accommodate a wide variety of unique MID sets.

In certain embodiments, each individual polynucleotide (e.g., double-stranded or single-stranded, as appropriate to the methodological details employed) in a sample to be analyzed is tagged with a unique MID so that the fate of each polynucleotide can be tracked in subsequent processes (where, as noted above, unique MID is meant to indicate that each different MID employed can be differentiated from every other MID employed by virtue of at least one characteristic, e.g., the nucleic acid sequence of the MID). For example (and as described below), having each nucleic acid tagged with a unique MID allows analysis of the sequence of each individual nucleic acid using the reflex sequence methods described herein. This allows the linkage of sequence information for large nucleic acid fragments that cannot be sequenced in a single sequencing run.

Reflex Sequence Process

As summarized above, aspects of the present invention include methods and compositions for moving a domain in a polynucleotide from a first location to a second location in the polynucleotide. An exemplary embodiment is shown in FIG. 1A.

FIG. 1A shows a single stranded polynucleotide 100 comprising, in a 5' to 3' orientation, a first domain (102; the domain to be moved); a reflex sequence 104; a nucleic acid sequence 106 having a site distal to the first domain (Site A), and a complement of the reflex sequence 108 (positioned at the 3' terminus of the polynucleotide). Nucleic acid sequence 106 may be from 30 bases to 30 kilobases in length. The steps of the reflex method described below will move the first domain into closer proximity to Site A. It is noted here that the prime designation in FIG. 1A denotes a complementary sequence of a domain. For example, First Domain' is the complement of the First Domain.

In Step 1, the reflex sequence and its complement in the polynucleotide are annealed intramolecularly to form polynucleotide structure 112, with the polynucleotide folding back on itself and hybridizing to form a region of complementarity (i.e., double stranded reflex/reflex' region). In this configuration, the 3' end of the complement of the reflex sequence can serve as a nucleic acid synthesis priming site. Nucleic acid synthesis from this site is then performed in extension Step 2 producing a complement of the first domain at the 3' end of the nucleic acid extension (shown in polynucleotide 114; extension is indicated with dotted arrow labeled "extend").

Denaturation of polynucleotide 114 (e.g., by heat) generates linear single stranded polynucleotide 116. As shown in FIG. 1, resultant polynucleotide 116 contains a complement of the first domain at a position proximal to Site A (i.e., separated by only the complement of the reflex sequence). This resultant polynucleotide may be used for any subsequent analysis or processing steps as desired by the user (e.g., sequencing, as a template for amplification (linear, PCR, etc.), sequence specific extraction, etc.).

In alternative embodiments, the first domain and reflex sequence are removed from the 5' end of the double-stranded region of polynucleotide 114 (shown in polynucleotide 118; removal is shown in the dotted arrow labeled "remove"). Removal of this region may be accomplished by any convenient method, including, but not limited to, treatment (under appropriate incubation conditions) of polynucleotide structure 114 with T7 exonuclease or by treatment with Lambda exonuclease; the Lambda exonuclease can be employed so long as the 5' end of the polynucleotide is phosphorylated. If the region is removed enzymatically, resultant polynucleotide 118 is used in place of polynucleotide 116 in subsequent steps (e.g., copying to reverse polarity).

In certain embodiments, polynucleotide 116 or 118 is used as a template to produce a double stranded polynucleotide, for example by performing a nucleic acid synthesis reaction with a primer that primes in the complement of the first domain. This step is sometimes referred to as copying to reverse polarity of a single stranded polynucleotide, and in some instances, the double-stranded intermediate product of this copying is not shown (see, e.g., FIG. 3). For example, copying to reverse the polarity of polynucleotide 116 results in single-stranded polynucleotide 120 having, in a 5' to 3' orientation, the first domain (122); the reflex sequence (124); the complement of polynucleotide 106 (oriented with the complement of Site A (Site A'; 126) proximal to the reflex sequence); the complement of the reflex sequence (128); and the complement of the first domain (130).

In certain embodiments, the first domain in the polynucleotide comprises one or more elements that find use in one or more subsequent processing or analysis steps. Such sequences include, but are not limited to, restriction enzyme sites, PCR primer sites, linear amplification primer sites, reverse transcription primer sites, RNA polymerase promoter sites (such as for T7, T3 or SP6 RNA polymerase), MID tags, sequencing primer sites, etc. Any convenient element can be included in the first domain and, in certain embodiments, is determined by the desires of the user of the methods described herein.

As an exemplary embodiment, suppose we want to sequence a specific polynucleotide region from multiple genomes in a pooled sample where the polynucleotide region is too long to sequence in a single reaction. For example, sequencing a polynucleotide region that is 2 kilobases or more in length using Roche 454 (Branford, Conn.) technology, in which the length of a single sequencing run is about 400 bases. In this scenario, we can design a set of left hand primers ($A_n$) and right hand primers ($B_n$) specific for the polynucleotide region that are positioned in such a way that we can obtain direct sequences of all parts of the insert, as shown in FIG. 1B. Note that the polynucleotide shown in FIG. 1B (140) has a domain (142) containing a primer site and an MID denoting from which original sample(s) the polynucleotide is derived. Site 142 thus represents an example of a First Domain site such identified as 122 in the FIG. 1A. The polynucleotide also includes a reflex site (144), which can be part of the polynucleotide region itself (e.g., a genomic sequence), added in a ligated adapter domain along with the primer site and the MID (an artificial sequence), or a combination of both (a sequence spanning the adapter/polynucleotide junction).

It is noted here that polynucleotide 140 can be categorized as a precursor to polynucleotide 100 in FIG. 1A, as it does not include a 3' reflex sequence complementary to the reflex site (domain 108 in FIG. 1A). As detailed below, polynucleotide 140 can be converted to a polynucleotide having the structural configuration of polynucleotide 100, a polynucleotide suitable as a substrate for the reflex process described herein (e.g., by primer extension using a $B_n$ primer and reversal of polarity).

In an exemplary embodiment, each $A_n$-$B_n$ primer pair defines a nucleic acid region that is approximately 400 bases in length or less. This size range is within the single-sequencing run read length of the current Roche 454 sequencing platform; a different size range for the defined nucleic acid region may be utilized for a different sequencing platform. Thus, each product from each reflex process can be sequenced in a single run. It is noted here that primer pairs as shown in FIG. 1B can be used to define regions 1 to 5 shown in FIG. 3 (described in further detail below).

In certain embodiments, to obtain the first part of the sequence of the polynucleotide region (i.e., in the original structure, that part of the polynucleotide closest to the first domain), we only need a right hand primer (e.g., $B_0$) and we do not need to transfer the MID as it is within reach of this sequencing primer (i.e., the MID is within 400 bases of sequencing primer $B_0$). All other $B_n$ primers have the reflex sequence added to their 5' ends ("R" element shown on B primers) so that they read 5' reflex-$B_n$. However, in certain embodiments, the $B_0$ primer does include the reflex sequence and is used in the reflex process (along with a corresponding $A_0$ primer) as detailed below.

As described above, we obtain a single stranded polynucleotide having, in the 5' to 3' orientation, a primer site (e.g., for Roche 454 sequencing), an MID, a reflex sequence and the polynucleotide to be sequenced. Numerous methods for obtaining single-stranded polynucleotides of interest have been described and are known in the art, including in U.S. Pat. No. 7,217,522, issued on May 15, 2007; U.S. patent application Ser. No. 11/377,462, filed on Mar. 16, 2006; and U.S. patent application Ser. No. 12/432,080, filed on Apr. 29, 2009; each of which is incorporated by reference herein in their entirety. For example, a single stranded product can be produced using linear amplification with a primer specific for the primer site of the template. In certain embodiments, the primer includes a binding moiety to facilitate isolation of the single stranded nucleic acid of interest, e.g., to immobilize the top strand on a binding partner of the binding moiety immobilized on a solid support. Removal of a hybridized, non-biotinylated strand by denaturation using heat or high pH (or any other convenient method) serves to isolate the biotinylated strand. Binding moieties and their corresponding binding partners are sometimes referred to herein as binding partner pairs. Any convenient binding partner pairs may be used, including but not limited to biotin/avidin (or streptavidin), antigen/antibody pairs, etc.

It is noted here that while the figures and description of the reflex process provided herein depict manipulations with regard to a single stranded polynucleotide, it is not necessarily required that the single stranded polynucleotide described or depicted in the figures be present in the sample in an isolated form (i.e., isolated from its complementary strand). In other words, double stranded polynucleotides may be used where only one strand is described/depicted, which will generally be determined by the user.

Figure 2:
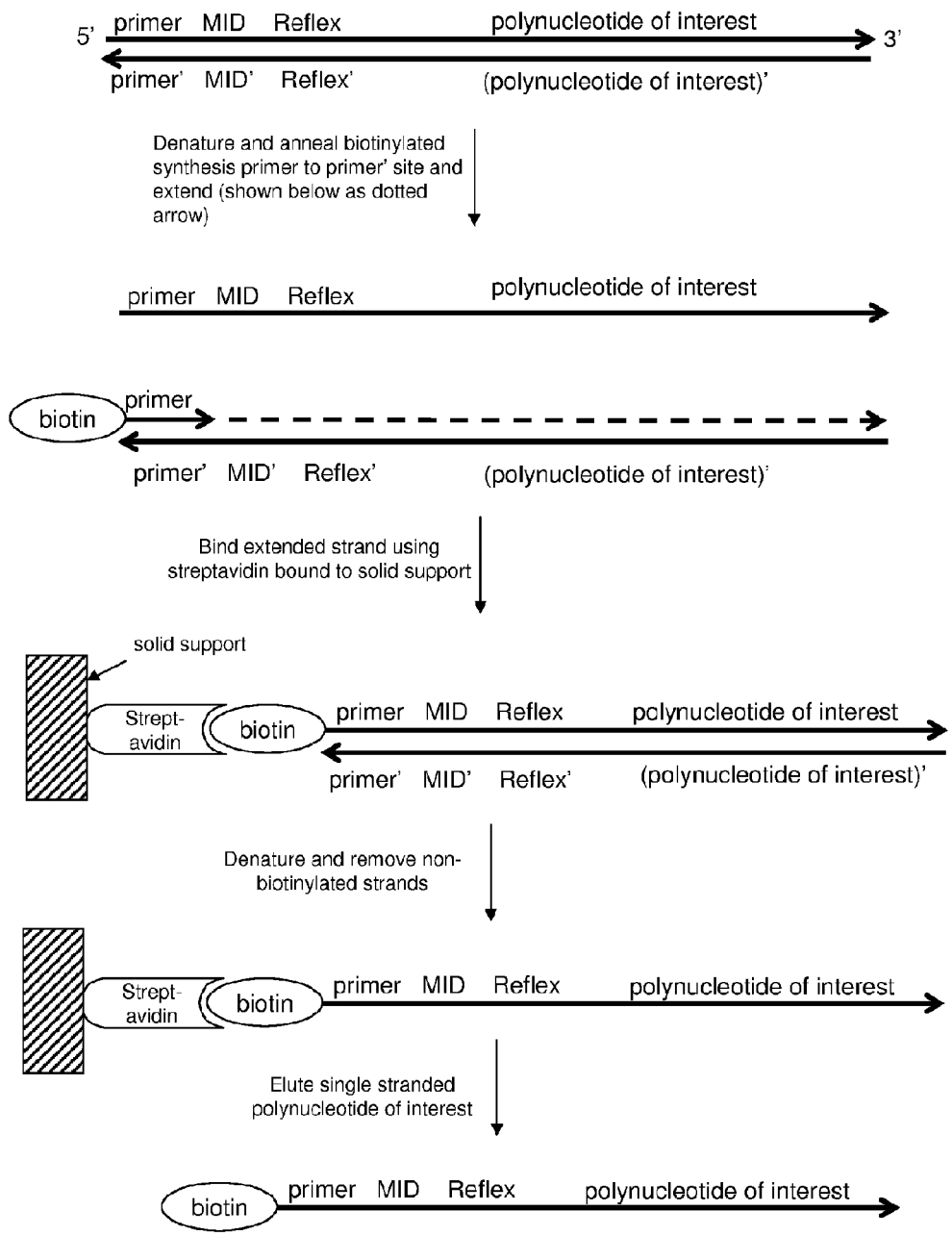
FIG. 2 shows an exemplary embodiment of using binding partner pairs (biotin/streptavidin) to isolate single stranded polynucleotides of interest.

The implementation of a single strand isolation step using the methods described above or variations thereof (or any other convenient single strand isolation step) will generally be based on the desires of the user. One example of isolating single stranded polynucleotides is shown in FIG. 2. In this Figure, a starting double stranded template (with 5' to 3' orientation shown as an arrow) is denatured and primed with a biotinylated synthesis primer specific for the primer site. After extension of the primer (i.e., nucleic acid synthesis), the sample is contacted with a solid support having streptavidin bound to it. The biotin moiety (i.e., the binding partner of streptavidin) on the extended strands will bind to the solid-phase streptavidin. Denaturation and washing is then performed to remove all non-biotinylated polynucleotide strands. If desired, the bound polynucleotide, which can be used in subsequent reflex process steps (e.g., as a template for $B_n$ primer extension reactions), may be eluted from the streptavidin support. Alternatively, the bound polynucleotide may be employed in subsequent steps of the desired process while still bound to the solid support (e.g., in solid phase extension reactions using $B_n$ primers). This process, with minor variations depending on the template being used and the identity of the desired single stranded polynucleotide, may be employed at any of a number of steps in which a single stranded product is to be isolated. It is noted that in certain embodiments, substrate bound biotinylated polynucleotide can be used to produce and isolate non-biotinylated single stranded products (i.e., by eluting the non-biotinylated products while leaving the biotinylated templates bound to the streptavidin on the solid support). Thus, the specifics of how binding partners are used to isolate single stranded polynucleotides of interest will vary depending on experimental design parameters.

Additional single-stranded isolation/production methods include asymmetric PCR, strand-specific enzymatic degradation, and the use of in-vitro transcription followed by reverse transcriptase (IVT-RT) with subsequent destruction of the RNA strand. As noted above, any convenient single stranded production/isolation method may be employed.

To the single stranded polynucleotide shown in FIG. 1B we anneal one of the $B_n$ primers having the appended reflex sequence, denoted with a capital "R" (e.g., $B_1$) and extend the primer under nucleic acid synthesis conditions to produce a copy of the polynucleotide that has a reflex sequence at its 5' end. A single stranded copy of this polynucleotide is then produced to reverse polarity using a primer specific for the primer site in the first domain' (complement of the first domain 102). The resulting nucleic acid has structure 100 shown in FIG. 1A, where the first domain 102 includes the primer site and the MID. Site A (110) in FIG. 1 is determined by the specificity of the 5' reflex-$B_n$ primer used.

The reflex process (e.g., as shown in FIG. 1) is then performed to produce a product in which the primer site and the MID are now in close proximity to the desired site (or region of interest (ROI)) within the original polynucleotide (i.e., the site defined by the primer used, e.g., $B_1$). The resulting polynucleotide can be used in subsequent analyses as desired by the user (e.g., Roche 454 sequencing technology).

It is noted here that, while not shown in FIGS. 1A and 1B, any convenient method for adding adapters to a polynucleotide to be processed as described herein may be used in the practice of the reflex process (adapters containing, e.g., primer sites, polymerase sites, MIDs, restriction enzyme sites, and reflex sequences). For example, adapters can be added at a particular position by ligation. For double stranded polynucleotides, an adapter can be configured to be ligated to a particular restriction enzyme cut site. Where a single stranded polynucleotide is employed, a double stranded adapter construct that possesses an overhang configured to bind to the end of the single-stranded polynucleotide can be used. For example, in the latter case, the end of a single stranded polynucleotide can be modified to include specific nucleotide bases that are complementary to the overhang in the double stranded adaptor using terminal transferase and specific nucleotides. In other embodiments, PCR or linear amplification methods using adapter-conjugated primers is employed to add an adapter at a site of interest. Again, any convenient method for producing a starting polynucleotide may be employed in practicing the methods of the subject invention.

In certain embodiments, the nucleic acid may be sequenced directly using a sequencing primer specific for the primer site. This sequencing reaction will read through the MID and desired site in the insert.

In certain embodiments, the polynucleotide may be isolated (or fractionated) using an appropriate $A_n$ primer (e.g., when using $B_1$ as the first primer, primer $A_1$ can be used). In certain embodiments, the $A_n$ primed polynucleotide is subjected to nucleic acid synthesis conditions to produce a copy of the fragment produced in the reflex process. In certain of these embodiments, the $A_n$ primer has appended on its 5' end a primer site that can be used in subsequent steps, including sequencing reactions. Providing a primer site in the $A_n$ primer allows amplifying and/or sequencing from both ends of the resultant fragment: from the primer site in the first domain 102 and the primer site in the $A_n$ primer (not shown in FIG. 1B). Because of the position of the primer sites and their distance apart (i.e., less than one sequencing run apart), sequencing from both ends will usually capture the sequence of the desired site (or ROI) and the sequence of the MID, which can be used for subsequent bioinformatic analyses, e.g., to positively identify the sample of origin. It is noted here that while sequencing in both directions is possible, it is not necessary, as sequencing from either primer site alone will capture the sequence of the ROI as well as its corresponding MID sequence.

Note that in certain embodiments, the first fragment obtained by amplification/extension from primer $B_0$ directly, the polarity of the ROI in the resulting fragment is reversed as compared to the ROI in fragments obtained by primers $B_1$-$B_n$. This is because the $B_0$-generated fragment, unlike the $B_1$-$B_n$ generated fragments, has not been subjected to a reflex process which reverses the orientation of the ROI sequence with respect to the first domain/reflex sequence (as described above). Therefore, the $B_0$ primer may have appended to it a primer site (e.g., at its 5' end) that can be used for subsequent amplification and/or sequencing reactions (e.g., in Roche 454 sequencing system) rather than a reflex sequence as with primers $B_1$-$B_n$. However, in certain embodiments, as noted above, the reflex process may be used with a corresponding $B_0$-$A_0$ primer pair as described above, i.e., using a $B_0$ primer having a 5' reflex sequence and a corresponding $A_0$ primer with its corresponding 5' adapter domain (e.g., a primer site).

It is noted here that because the particular sections of sequence to be analyzed are defined by the $A_n$-$B_n$ primer pairs (as shown and described above), a much higher sequence specificity is achieved as compared to using previous extraction methods that employ only a single oligo binding event (e.g., using probes on a microarray).

Figure 3:
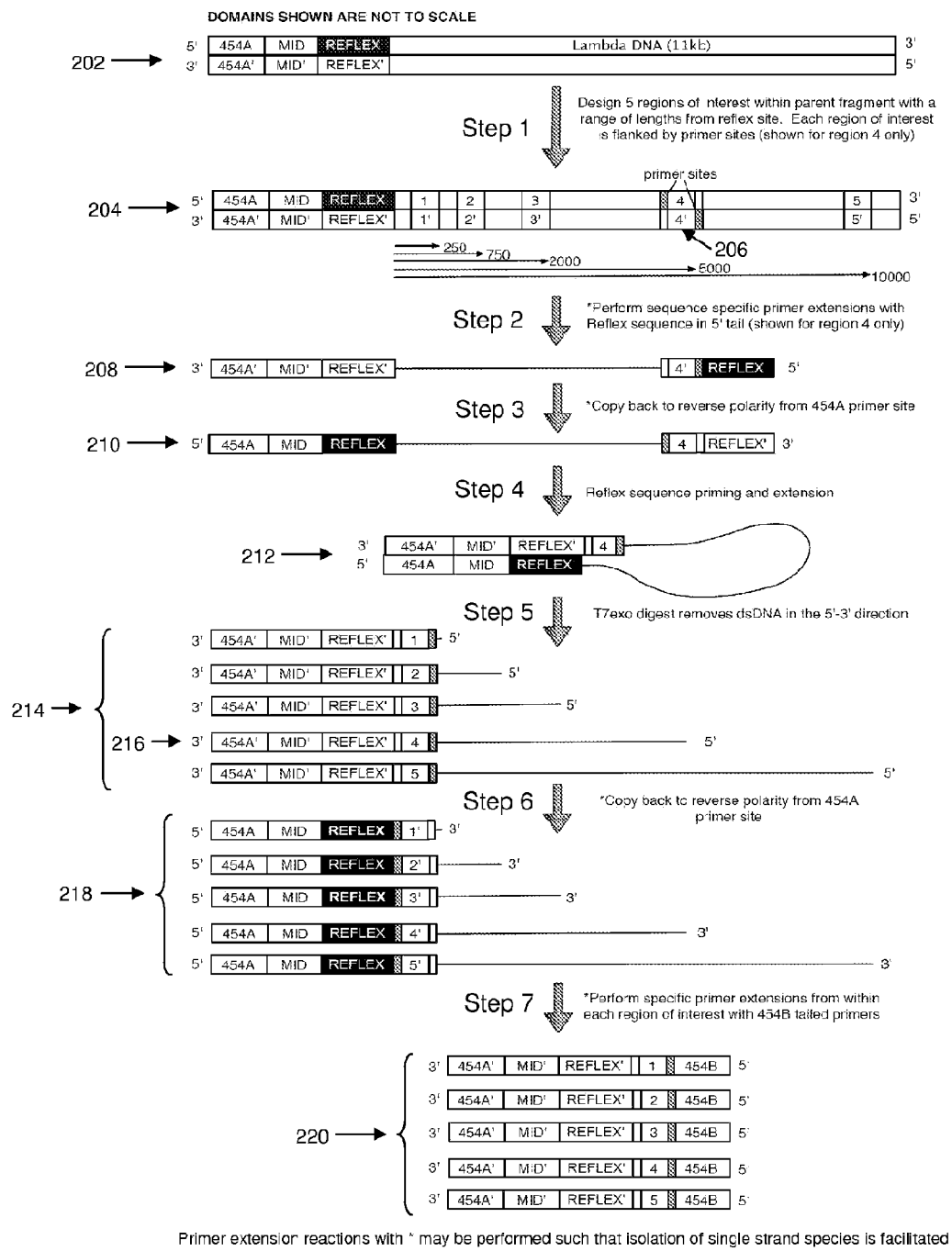
FIG. 3 is a schematic diagram illustrating an exemplary embodiment for moving a primer site and a MID to a specific location in a nucleic acid of interest.

FIG. 3 provides a detailed flow chart for an exemplary embodiment that employs reflex sequences for use in sequencing multiple specific regions in a polynucleotide (i.e., regions 1, 2, 3, 4 and 5 in an 11 kb region of lambda DNA).

A single parent DNA fragment 202 is generated that includes adapter domains (i.e., a Roche 454 sequencing primer site, a single MID, and a reflex sequence) and the sequence of interest. In the example shown, the sequence of interest is from lambda DNA and the reflex sequence is present on the top strand (with its complement shown in the bottom strand). Any convenient method for producing this parent DNA fragment may be used, including amplification with a primer that includes the adapter domains (e.g., using PCR), cloning the fragment into a vector that includes the adapter domains (e.g., a vector with the adapter domains adjacent to a cloning site), or by attaching adapters to polynucleotide fragments (e.g., fragment made by random fragmentation, by sequence-specific restriction enzyme digestion, or combinations thereof). While only a single fragment with a single MID is shown, the steps in FIG. 3 are applicable to samples having multiple different fragments each with a different MID, e.g., a sample having a population of homologous fragments from any number of different sources (e.g., different individuals). FIG. 3 describes the subsequent enzymatic steps involved in creating the five daughter fragments in which regions 1, 2, 3, 4 and 5 (shown in polynucleotide 204) are rearranged to be placed within a functional distance of the adapter domains (i.e., close enough to the adapter domains to be sequenced in a single Roche 454 sequencing reaction). Note that certain steps are shown for region 4 only (206).

In step 1, the five regions of interest are defined within the parent fragment (labeled 1 to 5 in polynucleotide 204) and corresponding primer pairs are designed for each. The distance of each region of interest from the reflex sequence is shown below polynucleotide 204. The primer pairs are designed as described and shown in FIG. 1B (i.e., the $A_n$-$B_n$ primer pairs). For clarity, only primer sites for region 4 are shown in FIG. 3 ("primer sites" surrounding region 4). In step 2, sequence specific primer extensions are performed (only region 4 is shown) with corresponding $B_n$ primers to produce single stranded polynucleotides having structure 208 (i.e., having the reflex sequence on the 5' terminus). As shown, the $B_n$ primer for region 4 will include a sequence specific primer site that primes at the 3'-most primer site noted for region 4 (where "3'-most" refers to the template strand, which in FIG. 3 is the top strand). This polynucleotide is copied back to produce polynucleotide 210 having reversed polarity (e.g., copied using a primer that hybridizes to the 454A' domain). Polynucleotide 210 has structure similar to polynucleotide 100 shown at the top of FIG. 1. Step 4 depicts the result of the intramolecular priming between the reflex sequence and its complement followed by extension to produce the MID' and 454A' structures at the 3' end (polynucleotide 212). In the embodiments shown in FIG. 3, polynucleotide 212 is treated with T7 exonuclease to remove double stranded DNA from the 5' end (as indicated above, this step is optional). The polynucleotide formed for region 4 is shown as 216 with polynucleotides for the other regions also shown (214).

It is noted here that the formation of each of the polynucleotides 214 may be accomplished either in separate reactions (i.e., structure with region 1 in proximity to the adapter domains is in a first sample, the structure with region 2 in proximity to the adapter region is in a second sample, etc.) or in one or more combined sample.

In step 6 the polynucleotides 214 are copied to reverse polarity to form polynucleotides 218. In step 7, each of these products are then primed with the second primer of the specific primer pair (see $A_n$ primers as shown in FIG. 1B) each having a second Roche 454 primer site (454B) attached at the 5' end, and extended to form products 220. Steps 6 and 7 may be combined (e.g., in a single PCR or other amplification reaction).

In summary, FIG. 3 shows how the reflex process can be employed to produce five daughter fragments 220 of similar length (e.g., ~500 bp) each of which contain DNA sequences that differ in their distance from the reflex sequence in the starting structure 202 while maintaining the original MID.

Figure 4:
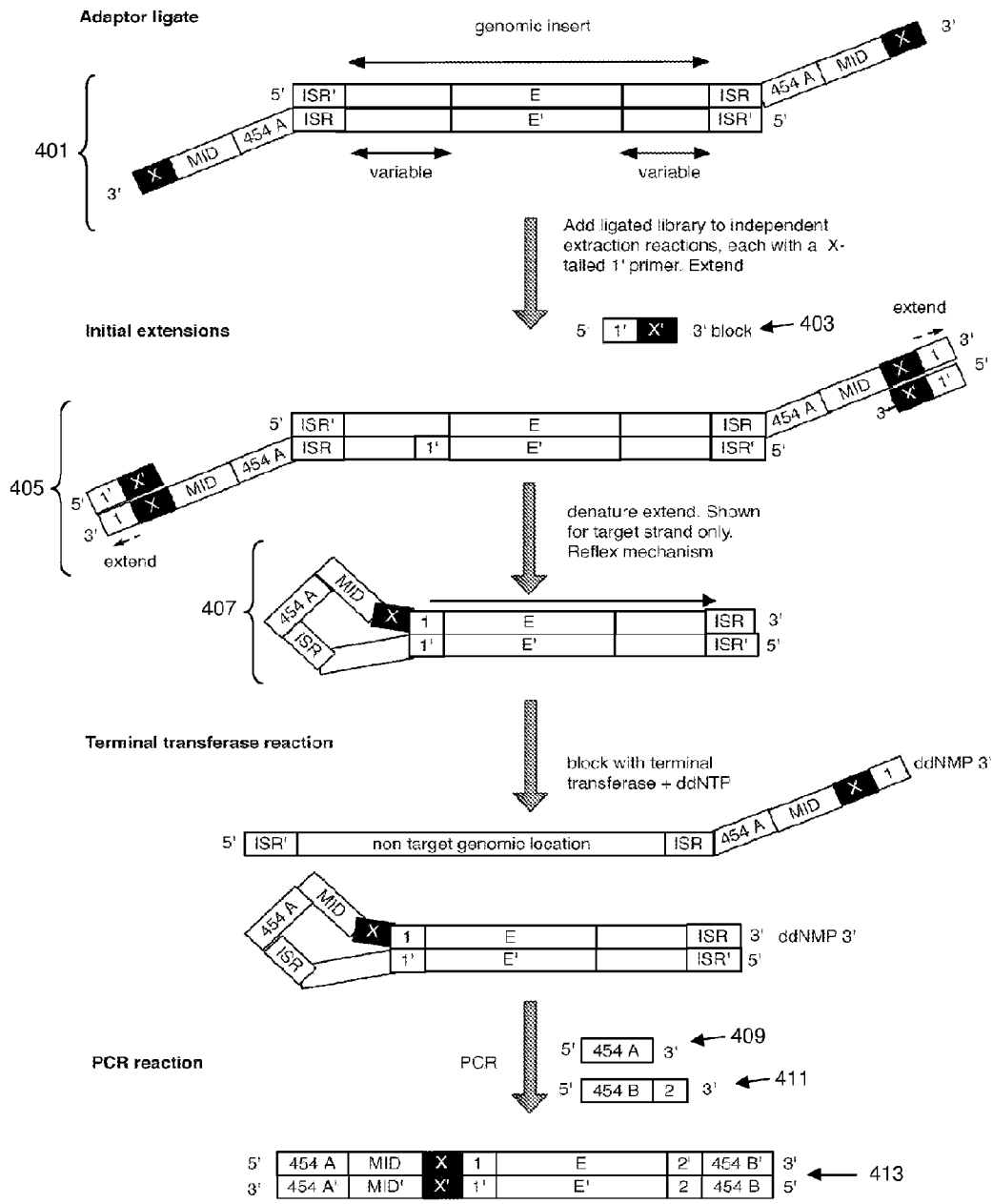
FIG. 4 shows a schematic diagram illustrating an exemplary use of the reflex process for generating a sample enriched for fragments having a region of interest (e.g., from a population of randomly fragmented and asymmetrically tagged polynucleotides).

FIG. 4 shows another exemplary use of the reflex process as described herein. In the embodiment shown in FIG. 4, a target sequence (i.e., containing region of interest "E") is enriched from a pool of adapter-attached fragments. In certain embodiments, the fragments are randomly sheared, selected for a certain size range (e.g., DNA having a length from 100 to 5000 base pairs), and tagged with adapters (e.g., asymmetric adapters, e.g., as described in U.S. patent application Ser. No. 12/432,080, filed on Apr. 29, 2009). The asymmetric adaptor employed in FIG. 4 contains a sequencing primer site (454A, as used in the Roche 454 sequencing platform), an MID, an X sequence, and an internal stem region (ISR), which denotes the region of complementarity for the asymmetric adapter that is adjacent to the adapter attachment site (see, e.g., the description in U.S. application Ser. No. 12/432,080, filed on Apr. 29, 2009, incorporated herein by reference in its entirety). The X sequence can be any sequence that can serve as a binding site for a polynucleotide containing the complement of the X sequence (similar to a primer site). As described below, the X sequence allows for the annealing of an oligonucleotide having a 5' overhang that can serve as a template for extension of the 3' end of the adaptor oligonucleotide. The sequencing direction of the sequencing primer site (454A primer site in structure 401 of FIG. 4) is oriented such that amplification of the adapter ligated fragment using the sequencing primer site proceeds away from the ligated genomic insert. This has the effect of making the initial asymmetric adapter ligated library 'inert' to amplification using this primer, e.g., in a PCR reaction.

To extract a region of interest (the "E" region), the library is mixed with an oligonucleotide (403) containing a 3' X' sequence and a target specific priming sequence (the 1' sequence) under hybridization/annealing conditions. The target specific sequence 1' is designed to flank one side of the region of interest (the 1' sequence adjacent to E in the genomic insert; note that only the E-containing polynucleotide fragment is shown in FIG. 4), much like a PCR primer. After annealing primer 403, the hybridized complex is extended, whereby all of the adaptor tagged fragments will obtain the complement of the target specific sequence (i.e., the 1 sequence) on the 3' end (see structure 405; arrows denote the direction of extension).

Extended products 405 are then denatured and the 1/1' regions allowed to hybridize intramolecularly in a reflex process priming event, after which nucleic acid extension is performed to form structure 407 (extension is from the 1 priming site; shown with an arrow). This reflex reaction creates a product (407) that, unlike its parent structure (405), has a sequencing primer site (454A) that is oriented such the extension using this primer sequence proceeds towards the region of interest. Thus, in the absence of a priming and extension reflex reaction, extension with a sequencing primer will not generate a product containing the region of interest (the E region). In other words, only E-region containing target polynucleotides will have a 454A sequence that can amplify genomic material (structure 407).

After completing the reflex process (using 1/1' as the reflex sequences), a PCR amplification reaction is performed to amplify the region of interest (with associated adapter domains). However, before performing the PCR reaction, the fragment sample is "inactivated" from further extension using terminal transferase and ddNTPs. This inactivation prevents non-target adaptor tagged molecules from performing primer extension from the 3' primer 1 site. Once inactivated, a PCR reaction is performed using a sequencing primer (i.e., 454A primer 409) and a second primer that primes and extends from the opposite side of the region of interest (i.e., primer 411, which includes a 5' 454B sequencing primer site and a 3' "2" region that primes on the opposite end of E from the 1 region). Only fragments that have undergone the reflex process and contain the E region will be suitable templates for the PCR reaction and produce the desired product (413).

Thus, the process exemplified in FIG. 4 allows for the movement of an adapter domain (e.g., containing functional elements and/or MID) into proximity to a desired region of interest.

The reflex process described herein can be used to perform powerful linkage analysis by combining it with nucleic acid counting methods. Any convenient method for tagging and/or counting individual nucleic acid molecules with unique tags may be employed (see, e.g., U.S. Pat. No. 7,537,897, issued on May 26, 2009; U.S. Pat. No. 7,217,522, issued on May 15, 2007; U.S. patent application Ser. No. 11/377,462, filed on Mar. 16, 2006; and U.S. patent application Ser. No. 12/432, 080, filed on Apr. 29, 2009; each of which is incorporated by reference herein in their). All of this can be conducted in parallel thus saving on the cost of labor, time and materials.

In one exemplary embodiment, a large collection of sequences is tagged with MID such that each polynucleotide molecule in the sample has a unique MID. In other words, each polynucleotide in the sample (e.g., each individual double stranded or single stranded polynucleotide) is tagged with a MID that is different from every other MID on every other polynucleotide in the sample. In general, to accomplish such molecular tagging the number of distinct MID tags to be used should be many times greater than the actual number of molecules to be analyzed. This will result in the majority of individual nucleic acid molecules being labeled with a unique ID tag (see, e.g., Brenner et al., Proc. Natl. Acad. Sci. USA. 2000 97(4):1665-70). Any sequences that then result from the reflex process on that particular molecule (e.g., as described above) will thus be labeled with the same unique MID tag and thus inherently linked. Note that once all molecules in a sample are individually tagged, they can be manipulated and amplified as much as needed for processing so long as the MID tag is maintained in the products generated.

For example, we might want to sequence one thousand viral genomes (or a specific genomic region) or one thousand copies of a gene present in somatic cells. After tagging each polynucleotide in the sample with a sequencing primer site, MID and reflex sequence (as shown in the figures and described above), we use the reflex process to break each polynucleotide into lengths appropriate to the sequencing procedure being used, transferring the sequencing primer site and MID to each fragment (as described above). Obtaining sequence information from all of the reflex-processed samples can be used to determine the sequence of each individual polynucleotide in the starting sample, using the MID sequence to defining linkage relationships between sequences from different regions in the polynucleotide being sequenced. Using a sequencing platform with longer read lengths can minimize the number of primers to be used (and reflex fragments generated).

Figure 5:
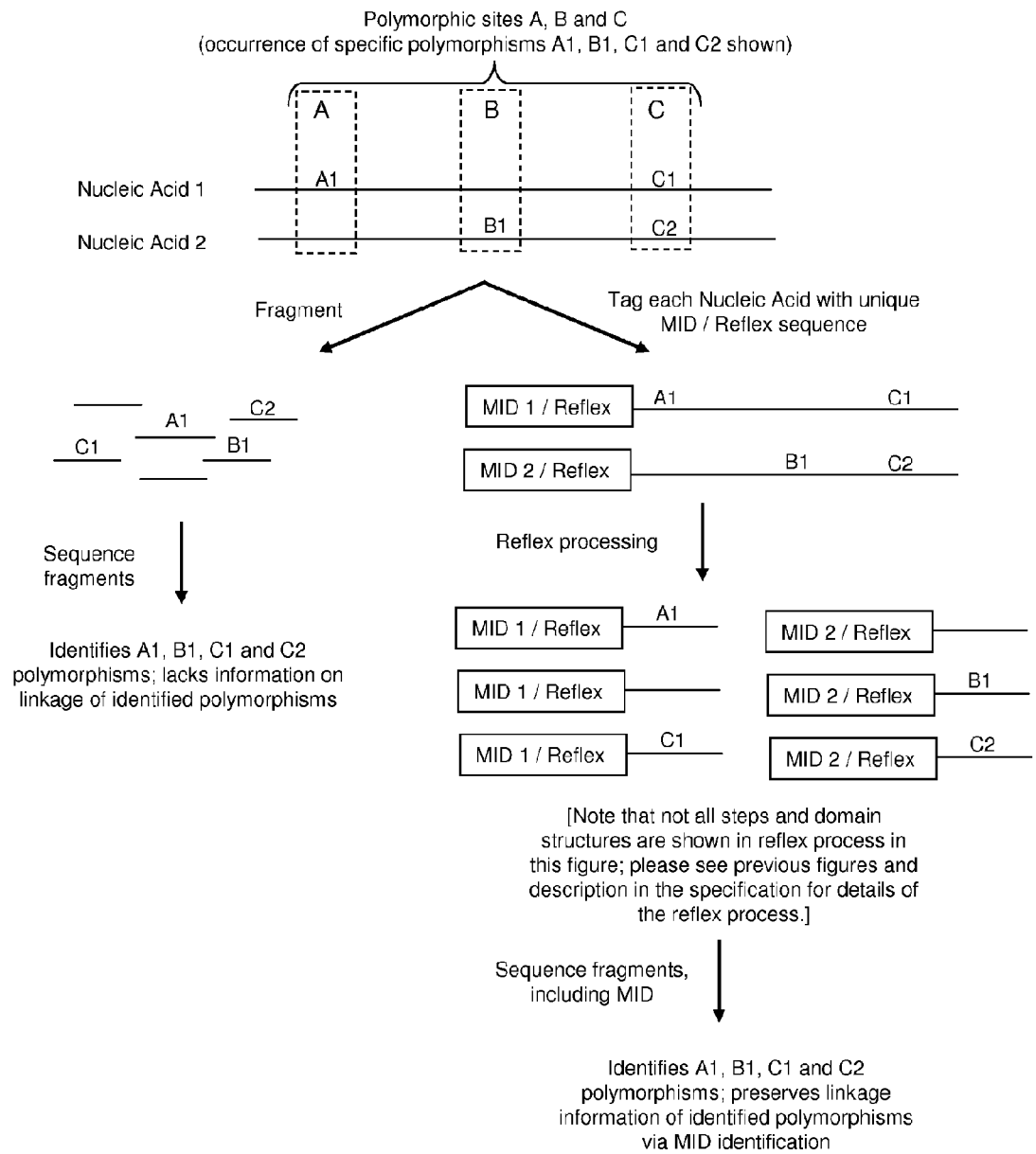
FIG. 5 shows a comparison of methods for identifying nucleic acid polymorphisms in homologous nucleic acids in a sample (e.g., the same region derived from a chromosomal pair of a diploid cell or viral genomes/transcripts). The top schematic shows two nucleic acid molecules in a sample (1 and 2) having a different assortment of polymorphisms in polymorphic sites A, B and C (A1, B1, C1 and C2). Standard sequencing methods using fragmentation (left side) can identify the polymorphisms in these nucleic acids but do not retain linkage information. Employing the reflex process described herein to identify polymorphisms (right side) maintains linkage information.

The advantages noted above are shown in FIG. 5. This figure shows a comparison of methods for identifying nucleic acid polymorphisms in homologous nucleic acids in a sample (e.g., the same region derived from a chromosomal pair of a diploid cell or viral genomes/transcripts). The top schematic shows two nucleic acid molecules in a sample (1 and 2) having a different assortment of polymorphisms in polymorphic sites A, B and C (A1, B1, C1 and C2). Standard sequencing methods using fragmentation (left side) can identify the polymorphisms in these nucleic acids but do not retain linkage information. Employing the reflex process described herein to identify polymorphisms (right side) maintains linkage information. It is noted that not all domain structures and steps are shown in the reflex process for simplicity.

Kits and Systems

Also provided by the subject invention are kits and systems for practicing the subject methods, as described above, such vectors configured to add reflex sequences to nucleic acid inserts of interest and regents for performing any steps in the cloning or reflex process described herein (e.g., restriction enzymes, nucleotides, polymerases, primers, exonucleases, etc.). The various components of the kits may be present in separate containers or certain compatible components may be precombined into a single container, as desired.

The subject systems and kits may also include one or more other reagents for preparing or processing a nucleic acid sample according to the subject methods. The reagents may include one or more matrices, solvents, sample preparation reagents, buffers, desalting reagents, enzymatic reagents, denaturing reagents, where calibration standards such as positive and negative controls may be provided as well. As such, the kits may include one or more containers such as vials or bottles, with each container containing a separate component for carrying out a sample processing or preparing step and/or for carrying out one or more steps of a nucleic acid variant isolation assay according to the present invention.

In addition to above-mentioned components, the subject kits typically further include instructions for using the components of the kit to practice the subject methods, e.g., to prepare nucleic acid samples for perform the reflex process according to aspects of the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

In addition to the subject database, programming and instructions, the kits may also include one or more control samples and reagents, e.g., two or more control samples for use in testing the kit.

Utility

The reflex process described herein provides significant advantages in numerous applications, a few of which are noted below (as well as described above).

For example, as described above, certain aspects of the reflex process define the particular sections of sequence to be analyzed by a primer pair, as in PCR (e.g., the two oligos shown as $A_n$-$B_n$ in FIG. 1B). This results in higher sequence specificity as compared to other extraction methods (e.g., using probes on a microarray) that only use a single oligo sequence. The separation of the probes defines a length that can be relatively uniform (hence making subsequent handling including amplification more uniform) and can also be tailored to the particular sequencing platform being employed.

Further, as described above, aspects of the present invention can be used to analyze homologous genomic locations in a multiplexed sample (i.e., a sample having polynucleotides from different genomic samples) in which the polynucleotides are tagged with the MID. This is possible because the reflex process, which operates intramolecularly, maintains the MID thus linking any particular fragment to the sample from which it originates.

Finally, as the reflex processes described herein function intramolecularly, one can determine the genetic linkage between different regions on the same large fragment that are too far apart to be sequenced in one sequence read. Such a determination of linkage may be of great value in plant or animal genetics (e.g., to decide if a particular set of variations are linked together on the same stretch of chromosome) or in viral studies (e.g., to determine if particular variations are linked together on the same stretch of a viral genome/transcripts, e.g., HIV, hepatitis virus, etc.).

EXAMPLES

Example I

Figure 6:
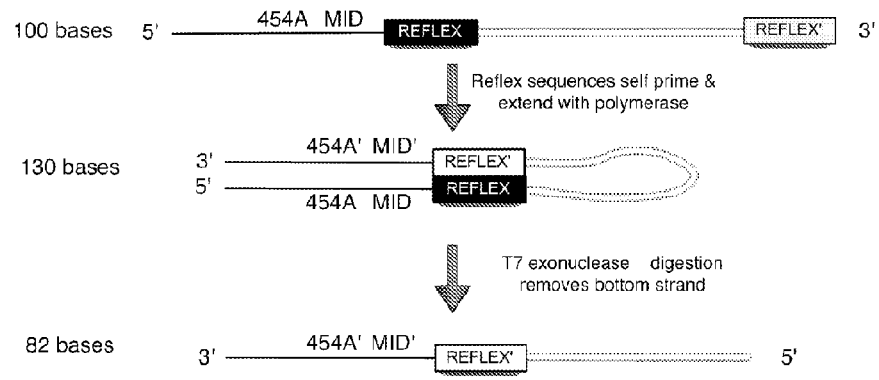
FIG. 6: Panel A is a schematic showing expected structures and sizes of nucleic acid species in the reflex process; Panel B is a polyacrylamide gel showing the nucleic acid species produced in the reflex process described in Example 1.
Figure 6:
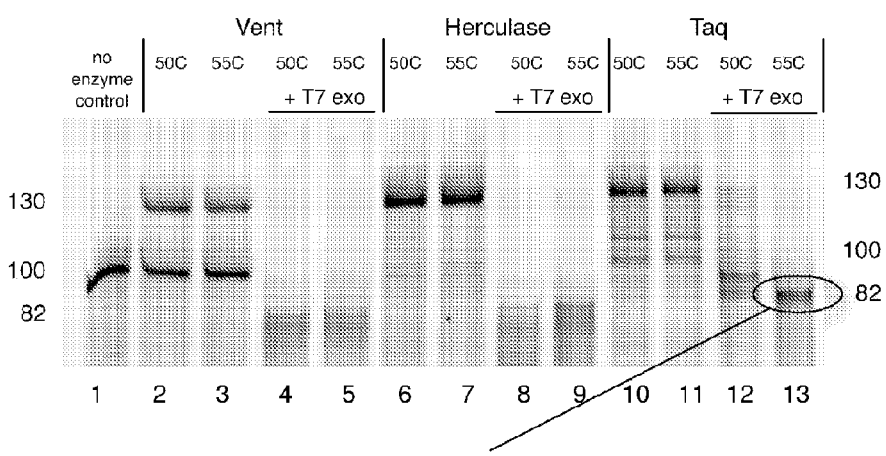
Figure 7:
FIG. 7: Panel A is a schematic showing the structure of the nucleic acid and competitor used in the reflex process; Panel B is a polyacrylamide gel showing the nucleic acid species produced in the reflex process described in Example 1.
Figure 7:
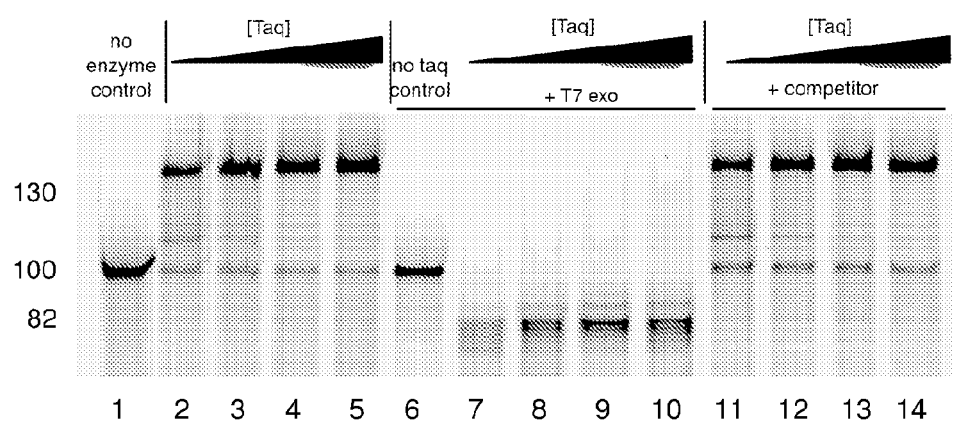

FIGS. 6 and 7 provide experimental data and validation of the reflex process described herein using synthetic polynucleotide substrates.

Methods

Substrate:

The 100 base oligonucleotide substrate (as shown diagrammatically in FIG. 6A) was synthesized with internal fluorescein-dT positioned between the REFLEX and REFLEX' sequences. This label provides convenient and sensitive method of detection of oligonucleotide species using polyacrylamide gel electrophoresis.

Extension Reactions:

Reactions were prepared which contained 1 µM of the 100 base oligonucleotide substrate, 200 µM dNTPs, presence or absence of 1 µM competitor oligonucleotide, 0.5 of each DNA polymerase ("DNAP"): Vent (NEB, 2 units/µl), Taq (Qiagen HotStarTaq 5 units/µl) and Herculase (Stratagene), and made up to 50 µl with the appropriate commercial buffers for each polymerase and dH$_2$O. For Taq titrations 0.5 µl, 1 µl, 2 µl, and 3 µl enzyme was used in the same 50 µl volume. Reactions were heated in a Biometra thermocycler to 95° C. for 15 minutes (Taq) or 5 minutes (Herculase, Vent), followed by 55° C. or 50° C. for 30 seconds, and a final incubation at 72° C. for 10 minutes.

T7 Exonuclease Digestions:

Reactions were prepared with 10 µl extension reactions above, 0.5 µl T7 exonuclease (NEB, 10 units/µl), and made up to 50 µl using NEB Buffer 4 and dH$_2$O. Reactions were incubated at 25° C. for 30 minutes.

Gel Electrophoresis analysis:

An 8% denaturing polyacrylamide gel was used to analyze reaction species. 0.4 of extension reactions, and 2 µl of digestion reactions were loaded and ran at 800V for ~1.5 hours. Gels were analyzed for fluorescein using an Amersham/General Electric Typhoon imager.

Results

FIG. 6A shows the structure of each stage of reflex sequence processing with the expected nucleic acid size shown on the left. The initial single stranded nucleic acid having a sequencing primer site (the Roche 454 sequencing primer A site; listed as 454A); an MID; a reflex sequence; the insert; and a complement of the reflex sequence is 100 nucleotides in length. After self-annealing and extension, the product is expected to be 130 nucleotides in length. After removal of the double stranded region from the 5' end, the nucleic acid is expected to be 82 bases in length.

FIG. 6B shows the results of three experiments using three different nucleic acid polymerases (Vent, Herculase and Taq, indicated at the top of the lanes). The temperature at which the annealing was carried out is shown at the top of each lane (either 50° C. or 55° C.). The sizes of the three nucleic acids as noted above are indicated on the left and right side of the gel.

As shown in FIG. 6B, extension appears to be most efficient under the conditions used with Herculase (Herculase is a mixture of two enzymes: modified Pfu DNAP and Archaemax (dUTPase)). Most (or all) of the initial 100 base pair nucleic acid are converted to the 130 base pair product (see lanes 6 and 7). However, after T7 exonuclease digestion the 3'-5' exonuclease activity of Herculase results in partial digestion of the desired 82 base product (note bands at and below the 82 base pairs in lanes 8 and 9).

Taq, which lacks 3'-5' exonuclease activity, shows a stronger band at the expected size of the final product after T7 exonuclease digestion (see lane 13).

FIG. 7 shows the effect on the reflex process of increasing amounts of Taq polymerase as well as the use of a reflex sequence competitor (schematically shown in FIG. 7A).

As shown in lanes 2 to 5, increased Taq concentration improves extension to ~90% conversion of the starting nucleic acid (see lane 5). Lanes 7 to 8 show that T7 exonuclease digestion does not leave a perfect 82 base product. This may be due to collapse of dsDNA when T7 exonuclease has nearly completed its digestion from the 5' end in the double stranded region of the fold-back structure. It is noted that in many embodiments, the removal of a few additional bases from the 5' end of the polynucleotide will not interfere with subsequent analyses, as nucleotide bases at the 5' end are often removed during subsequent steps.

As shown in Lanes 11-14, addition of a competitor (which can interfere with annealing of the reflex sequences to form the fold-back structure) results in only a small decrease (~5-10%) of fully extended product. Thus, as expected, the intramolecular reaction is heavily favored. Although not shown, we have observed that the competitor oligonucleotide also gets extended by the same amount (~5-10%). The concentration of the competitor, the concentration of the reflex substrate, and the overall genetic complexity, will all likely affect specific results. The experiments shown in FIGS. 6 and 7 demonstrate that the core parts of the reflex processes as described herein is functional and can be implemented.

Example II

Figure 8:
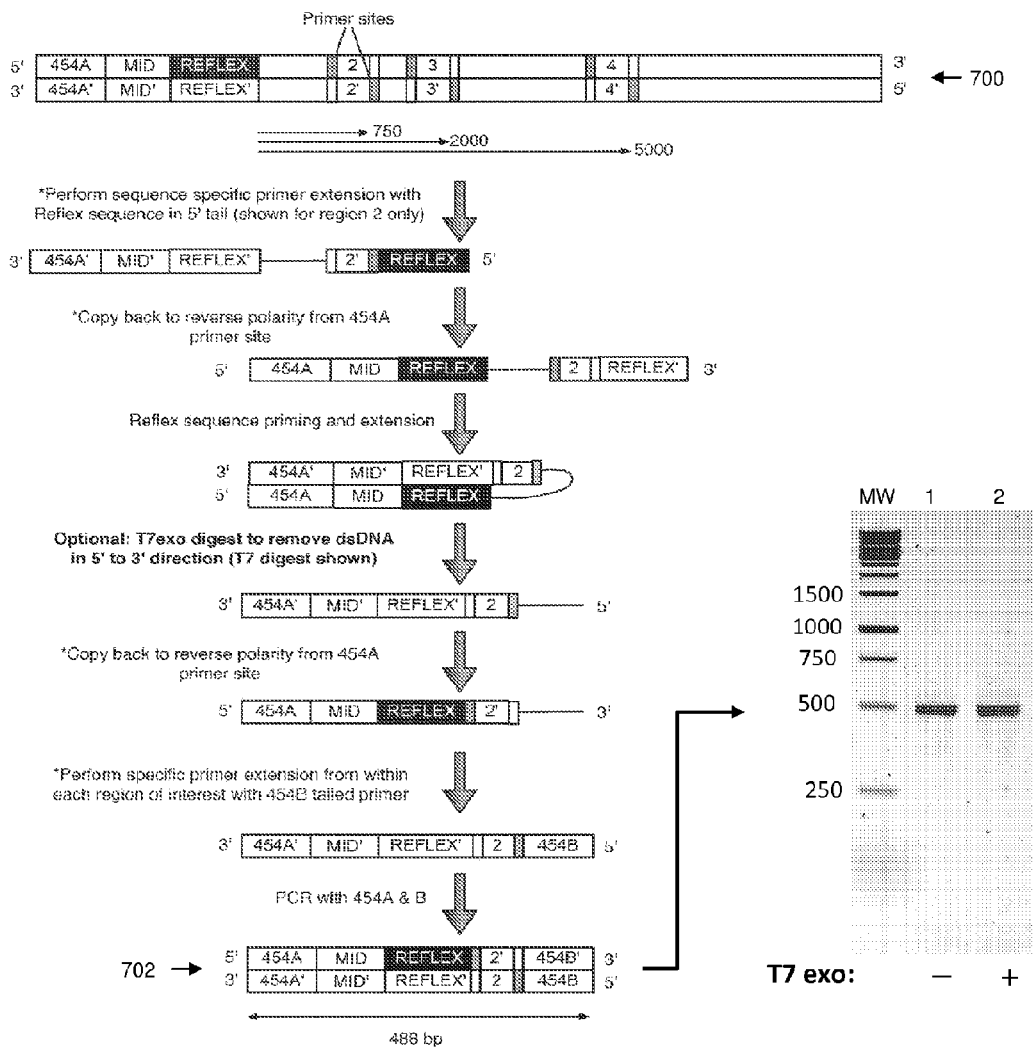
FIG. 8 shows a flow chart of a reflex process (left) in which the T7 exonuclease step is optional. The gel on the right shows the resultant product of the reflex process either without the T7 exonuclease step (lane 1) or with the T7 exonuclease step (lane 2).

FIG. 8 shows the reflex workflow (diagram at left) and exemplary results of the workflow (gel at right) for a specific region of interest (ROI). The starting material is a double stranded nucleic acid molecule (700) that contains a 454A primer site, an MID, a reflex site, and a polynucleotide of interest having three ROIs (2, 3 and 4) at different locations therein. This starting material was subjected to reflex processes (as described in above) specific for ROI 2 as shown in the diagram at the left of the figure, both with and without the use of a T7 exonuclease step (the T7 exonuclease step is shown in the diagram is indicated as "Optional").

Completion of all steps shown in the reflex process should result in a double stranded polynucleotide of 488 base pairs (702) with or without the T7 exonuclease step.

As shown in the gel on the right of FIG. 8, the 488 base pair product was produced in reflex processes with and without the T7 exonuclease step.

Figure 9:
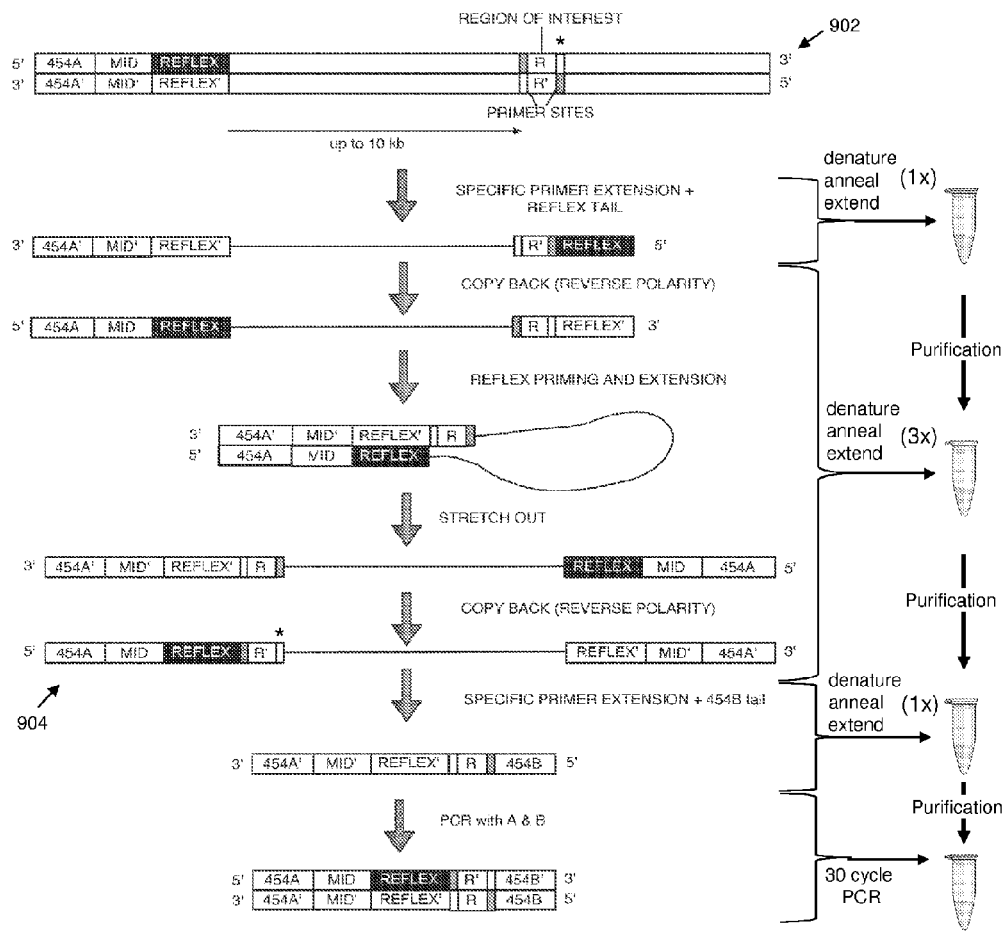
FIG. 9 shows an exemplary reflex process workflow with indications on the right as to where purification of reaction products is employed (e.g., using Agencourt beads to remove primer oligos).

FIG. 9 shows an exemplary protocol for a reflex process based on the results discussed above. The diagram shows specific reflex process steps with indications on the right as to where purification of reaction products is employed (e.g., using Agencourt SPR1 beads to remove primer oligos). One reason for performing such purification steps is to reduce the potential for generating side products in a reaction (e.g., undesirable amplicons). While FIG. 9 indicates three purification steps, fewer or additional purification steps may be employed depending on the desires of the user. It is noted that the steps of reversing polarity, reflex priming and extension, and "stretch out" (or denaturation)/second reversing polarity step can be performed without intervening purification steps.

The protocol shown in FIG. 9 includes the following steps:
annealing a first primer containing a 5' reflex sequence (or reflex tail, as noted in the figure) specific for the 3' primer site for the R' region to the starting polynucleotide and extending (the primer anneals to the top strand at the primer site at the right of R in polynucleotide 902, indicated with a *; this step represents the first denature, anneal and extend process indicated on the right);

after purification, adding a 454A primer and performing three cycles of denaturing, annealing and extending: the first cycle results in the copy-back from the 454A primer to reverse the polarity of the strand just synthesized; the second cycle breaks apart the double stranded structure produced, allows the reflex structure to form and then extend; the third cycle results in another copy-back using the same 454A primer originally added;

after purification, adding a second primer specific for the second primer site for the R' region having a 5' 454B tail (this primer anneals to the primer site 3' of the R' region in polynucleotide 904, indicated with a *) and denaturing, annealing and extending resulting in a polynucleotide product having 454A and 454B sites surrounding the MID, the reflex sequence, and R'. Note that the first primer specific for the R' region and the second primer specific for the R' region define its boundaries, as described above and depicted in FIG. 1B);

after another purification, adding 454A and 454B primers and performing a PCR amplification reaction.

Example III

As described above, a reflex sequence can be an "artificial" sequence added to a polynucleotide as part of an adapter or can be based on a sequence present in the polynucleotide of interest being analyzed, e.g., a genomic sequence (or "non-artificial").

The data shown in prior Examples used "artificial" reflex sites. In this Example, the reflex site is a genomic sequence present in the polynucleotide being analyzed.

The starting material is a double stranded DNA containing a 454A site, an MID and a polynucleotide to be analyzed. The 454A and MID were added by adapter ligation to parent polynucleotide fragments followed by enrichment of the polynucleotide to be analyzed by a hybridization-based pullout reaction and subsequent secondary PCR amplification (see Route 1 in FIG. 13). Thus, the reflex site employed in this example is a sequence normally present at the 5' end of the subject polynucleotide (a genomic sequence). The polynucleotide being analyzed includes a region of interest distal to the 454A and MID sequences that is 354 base pairs in length.

This starting double stranded nucleic acid is 755 base pairs in length. Based on the length of each of the relevant domains in this starting nucleic acid, the reflex process should result in a product of 461 base pairs.

Figure 10:
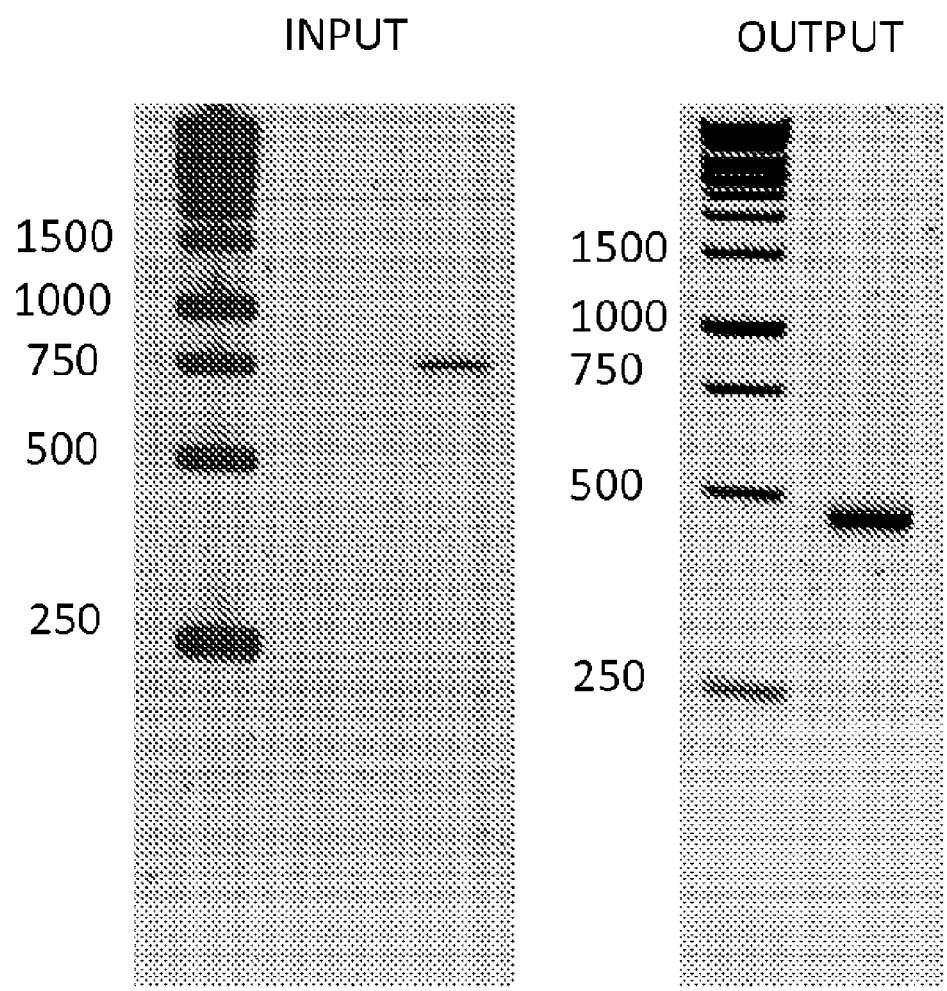
FIG. 10 shows the starting material (left panel) and the resultant product generated (right panel) using a reflex process without using a T7 exonuclease step (as described in Example II). The reflex site in the starting material is a sequence normally present in the polynucleotide being processed (also called a "non-artificial" reflex site). This figure shows that the 755 base pair starting nucleic acid was processed to the expected 461 base pair product, thus confirming that a "non-artificial" reflex site is effective in transferring an adapter domain from one location to another in a polynucleotide of interest in a sequence specific manner.

FIG. 10 shows the starting material for the reflex process (left panel) and the resultant product generated using the reflex process (right panel; reflex process was performed as described in Example II, without using a T7 exonuclease step). A size ladder is included in the left hand lane of each gel to allow estimation of the size of the test material. This figure shows that the 755 base pair starting nucleic acid was processed to the expected 461 base pair product, thus confirming that a "non-artificial" reflex site is effective in moving an adapter domain from one location to another in a polynucleotide of interest in a sequence specific manner.

Example IV

Figure 11:
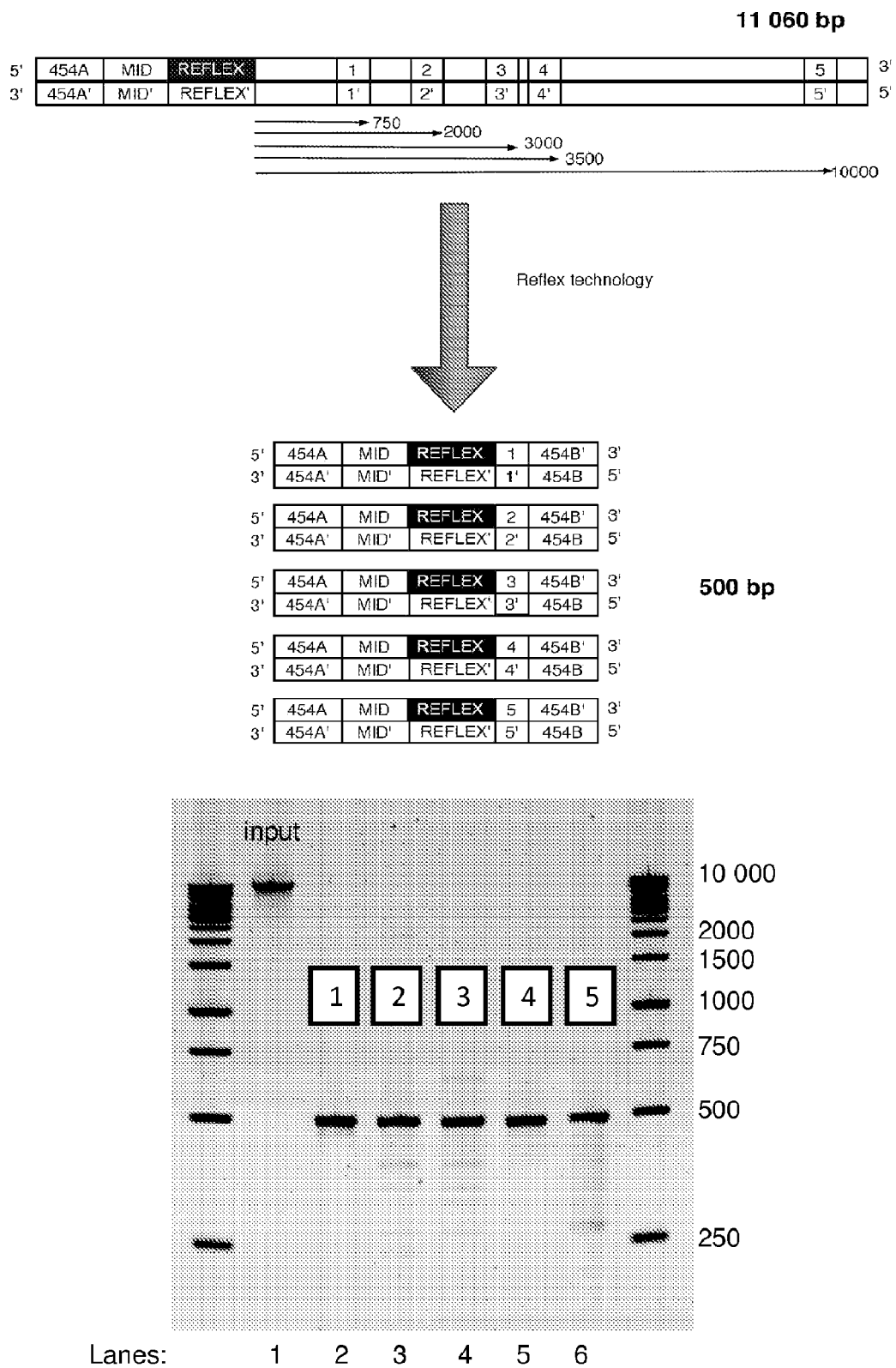
FIG. 11 shows a schematic and results of an experiment in which the reflex process is performed on a single large initial template (a "parent" fragment) to generate five different products ("daughter" products) each having a different region of interest (i.e., daughter products are produced having either region 1, 2, 3, 4 or 5).

FIG. 11 shows a schematic of an experiment in which the reflex process is performed on a single large initial template (a "parent" fragment) to generate 5 different products ("daughter" products) each having a different region of interest (i.e., daughter products are produced having either region 1, 2, 3, 4 or 5). The schematic in FIG. 11 shows the starting fragment (11,060 base pairs) and resulting products (each 488 base pairs) generated from each of the different region of interest-specific reflex reactions (reflex reactions are performed as described above). The panel (gel) on the bottom of FIG. 11 shows the larger starting fragment (Lane 1) and the resulting daughter products for each region-specific reflex reaction (lanes 2 to 6, with the region of interest noted in each in the box), where the starting and daughter fragments have the expected lengths. Sequencing of the products confirmed the identity of the region of interest in each of the reflex products shown in the gel. These results demonstrate that multiple different reflex products can be generated from a single, asymmetrically tagged parent fragment while maintaining the adapter domains (e.g., the primer sites and MID).

Example V

Figure 12:
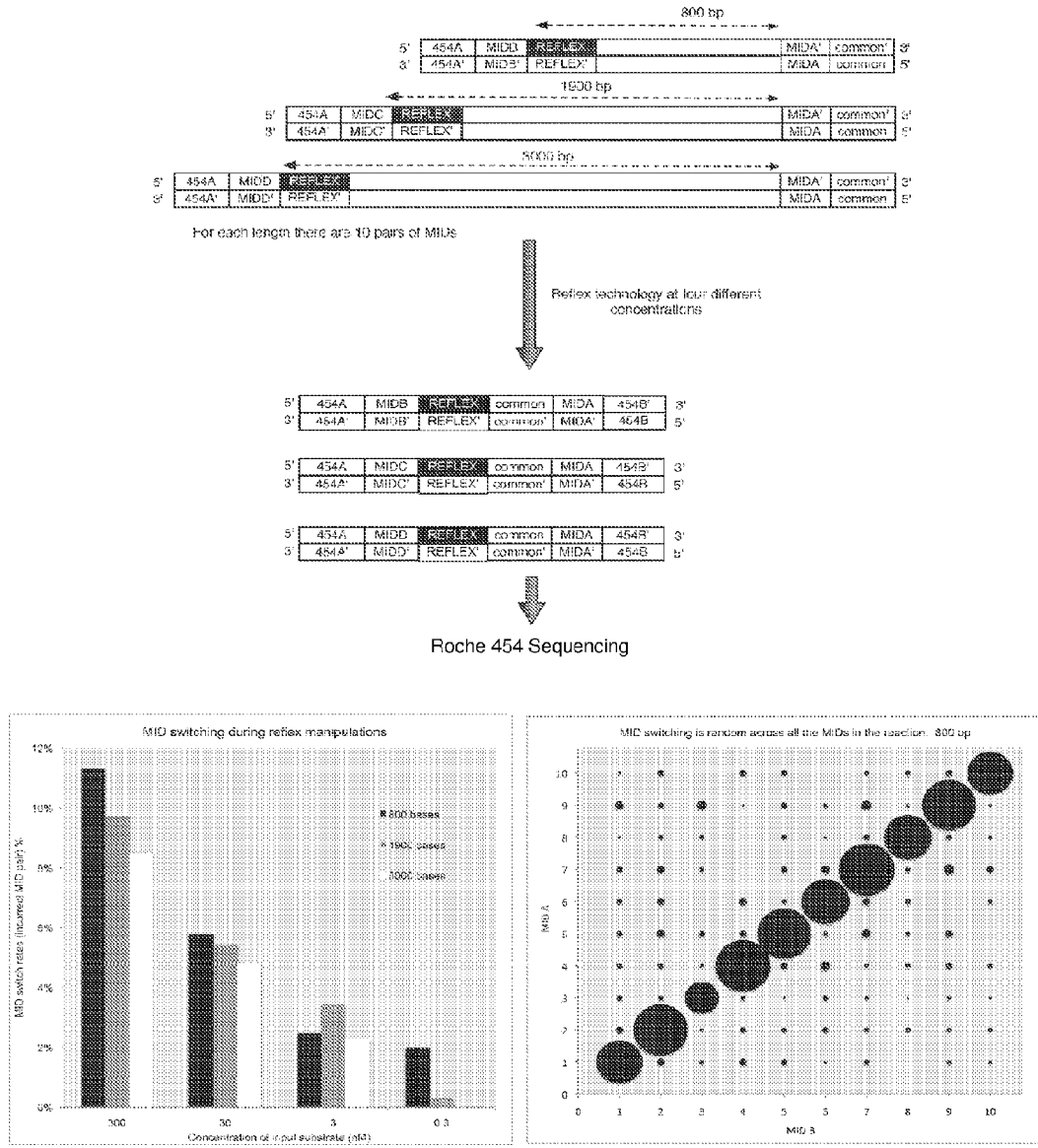
FIG. 12 shows a schematic and results of experiments performed to determine the prevalence of intramolecular rearrangement during the reflex process (as desired) vs. intermolecular rearrangement (MID switching).

FIG. 12 details experiments performed to determine the prevalence of intramolecular rearrangement (as desired in the reflex process) vs. intermolecular rearrangement. Intermolecular rearrangement is undesirable because it can lead to the transfer of an MID from one fragment to another (also called MID switching). MID switching can occur if a reflex sequence in a first fragment hybridizes to its complement in a second fragment during the reflex process, leading to appending the MID from the second fragment to the first fragment. Thus, intermolecular rearrangement, or MID switching, should be minimized to prevent the transfer of an MID from one fragment in the sample to another, which could lead to a misrepresentation of the source of a fragment.

To measure the prevalence of MID switching under different reflex conditions, fragments having different sizes were generated that included two different MIDs, as shown in the top panel of FIG. 12. The common sequence on these fragments serves as the priming site for the first extension reaction to add the second reflex sequence (see, e.g., step 2 of FIG. 3). Three exemplary fragments are shown in FIG. 12 for each different fragment size (i.e., 800 base pairs with an MIDB and MIDA combination; 1900 base pairs with MIDC and MIDA combination; and 3000 base pairs with MIDD and MIDA combination). For each MID family (A, B, C and D), there are 10 different members (i.e., MIDA had 10 different members, MIDB has 10 different members, etc.). A set of 10 dual MID fragments for each different size fragment (i.e., 800, 1900 and 3000 base pairs) were generated, where the MID pairs (i.e., MIDA/MIDB, MIDA/MIDC, and MIDA/MIDD) were designated as 1/1, 2/2, 3/3, 4/4, 5/5, 6/6, 7/7, 8/8, 9/9, and 10/10. All 10 fragments of the same size were then mixed together and a reflex protocol was performed.

Due to the domain structure of the fragments, a successful reflex process results in the two MIDs for each fragment being moved to within close enough proximity to be sequenced in a single read using the Roche 454 sequencing platform (see the reflex products shown in the schematic of FIG. 12). The reflex reactions for each fragment size were performed at four different fragment concentrations to determine the effect of this parameter, as well as fragment length, in the prevalence of MID switching. The reflex products from each reaction performed were subjected to 454 sequencing to determine the identity of both MIDs on each fragment, and thereby the proportion of MID switching that occurred.

The panel on the bottom left of FIG. 12 shows the rate of MID switching (Y axis, shown in % incorrect (or switched) MID pair) for each different length fragment at each different concentration (X axis; 300, 30, 3 and 0.3 nM). As shown in this panel, the MID switch rate decreases with lower concentrations, as would be expected, because intermolecular, as opposed to intramolecular, binding events are concentration dependent (i.e., lower concentrations lead to reduced intermolecular hybridization/binding). In addition, the MID switch rate decreases slightly with length. This is somewhat unexpected as the ends of longer DNA fragments are effectively at a lower concentration with respect to one another. The reasons for why we do not see this is probably because the production of reflex priming intermediates continues during the final PCR, which means that reflex priming reactions are happening continuously which contributes to MID switching. It is probably the case that the shorter reflex products are able to undergo a higher rate of 'background' reflexing, and therefore increase the overall MID switch rate a little.

These results demonstrate that MID switching can be minimized (e.g., to below 2%, below 1% or even to nearly undetectable levels) by altering certain parameters of the reaction, e.g., by reducing fragment concentration and/or fragment length.

The panel on the bottom right of FIG. 12 shows the frequency of MID switching in the reflex process for the 800 base pair fragments (i.e., MIDA/MIDB containing fragments). In this figure, the area of each circle is proportional to the number of reads containing the corresponding MIDA and MIDB species (e.g., MIDA1/MIDB1; MIDA1/MIDB2; etc.). Thus, a circle representing 200 reads will be 40 times larger in terms of area than a circle representing 5 reads.

As noted above, the MIDA/MIDB combinations having the same number (shown on the X and Y axis, respectively) represent the MIDA/MIDB combinations present in the sample prior to the reflex process being performed (i.e., MIDA/MIDB combinations 1/1, 2/2, 3/3, 4/4, 5/5, 6/6, 7/7, 8/8, 9/9, and 10/10 were present in the starting sample). All other MIDA/MIDB combinations identified by Roche 454 sequencing were the result of MID switching.

This figure shows that the MID switching that occurs during the reflex process is random, i.e., that MID switching is not skewed based on the identity of the MIDs in the reaction).

Exemplary Reflex Protocols

Figure 13:
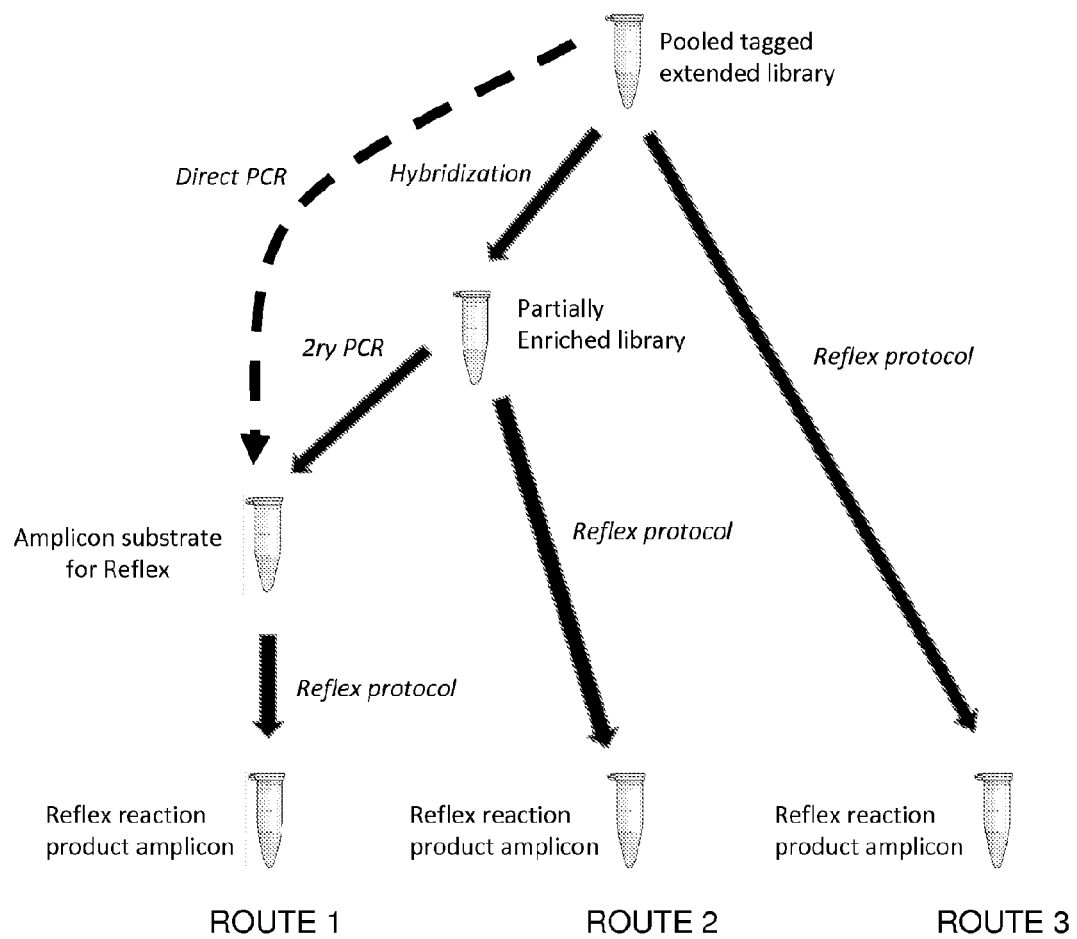
FIG. 13 shows a diagram of exemplary workflows for preparing material for and performing the reflex process.

FIG. 13 shows a diagram of exemplary protocols for performing the reflex process on pools of nucleic acids, for example, pools of nucleic acids from different individuals, each of which are labeled with a unique MID. In Route 3, a pooled and tagged extended library is subjected directly to a reflex process. In Route 2, the pooled library is enriched by target-specific hybridization followed by performing the reflex process. In Route 1 employs enrichment by PCR amplification. As shown in FIG. 13, PCR enrichment can be performed directly on the pooled tagged extended library or in a secondary PCR reaction after a hybridization-based enrichment step has been performed (as in Route 2) to generate an amplicon substrate that is suitable for the reflex process. Additional routes for preparing a polynucleotide sample for performing a reflex process can be implemented (e.g., having additional amplification, purification, and/or enrichment steps), which will generally be dependent on the desires of the user.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

The invention claimed is:

1. A method of sample analysis, comprising:
a) annealing a reflex sequence in a polynucleotide strand in a sample with a complement of the reflex sequence present in the polynucleotide strand, wherein the polynucleotide strand comprises the following in a 5' to 3' orientation:
a first domain comprising i. a primer site and ii. a multiplex identifier (MID) comprising a unique nucleotide sequence that distinguishes said polynucleotide strand from other polynucleotide strands in said sample;
the reflex sequence;
a polynucleotide of interest that is from 100 bases to 30 kilobases in length, wherein said polynucleotide of interest has a desired site that is distal to the first domain; and
the complement of the reflex sequence, wherein the complement of the reflex sequence is present at the 3' end of the polynucleotide strand;
b) extending from the 3' end of the complement of the reflex sequence through the first domain to produce a double stranded region comprising a complement of the first domain at the 3' end of the extended polynucleotide strand, thereby moving the first domain into proximity with the desired site; and
c) sequencing the MID and the desired site using a primer that is complementary to the primer site in the complement of the first domain.

2. The method of claim 1, wherein the reflex sequence is from 10 to 50 nucleotides in length.

3. The method of claim 1, wherein the first domain comprises an RNA polymerase site.

4. The method of claim 1, the method further comprising removing the first domain and the reflex sequence from the 5' end of the double stranded region.

5. The method of claim 4, wherein the removing step comprises treating the nucleic acid of step b with T7 exonuclease.

6. The method of claim 1, wherein the first domain is present in an adapter region attached to the polynucleotide of interest.

7. The method of claim 6, wherein the reflex sequence is present in the adapter region.

8. The method of claim 6, wherein the reflex sequence is a sequence present within the 5' region of the polynucleotide of interest.

9. The method of claim 1, wherein the sample is a multiplexed sample, wherein the first domain in each of the polynucleotide strands in the multiplexed sample comprises a MID corresponding to its parental sample.

10. The method of claim 1, wherein the sample comprises multiple polynucleotide strands, and wherein each polynucleotide strand in the sample comprises a unique MID in the first domain.

11. The method of claim 1, wherein the polynucleotide strand is produced by:
annealing a nucleic acid synthesis primer to a parent polynucleotide strand, wherein the parent polynucleotide strand comprises the following in a 5' to 3' orientation:
the first domain;
the reflex sequence; and
a second domain comprising the polynucleotide of interest;
wherein the nucleic acid synthesis primer comprises:
a 3' priming domain that is complementary to a site adjacent to and 3' of the polynucleotide of interest in the second domain; and
a 5' reflex sequence;
extending the nucleic acid synthesis primer to produce an extension product; and
replicating the resultant extension product with a second nucleic acid synthesis primer that anneals at the 3' end of the complement of the first domain, thereby producing the polynucleotide strand.

12. The method of claim 11, wherein the parent polynucleotide strand is enriched prior to the annealing step based on its sequence.

13. The method of claim 1, further comprising the steps of:
c) replicating the polynucleotide strand of step b with a first nucleic acid synthesis primer that anneals at the 3' end of the complement of the first domain to produce a first extension product;
d) annealing a second nucleic acid synthesis primer to the first extension product, wherein the second nucleic acid synthesis primer comprises a 3' priming domain that is complementary to a site within the polynucleotide of interest in the first extension product; and
e) extending the second synthesis primer to produce a second extension product.

14. The method of claim 13, wherein the second synthesis primer comprises a 5' domain that is not complementary to the polynucleotide of interest in the first extension product.

15. The method of claim 14, wherein the first domain comprises a first primer site and the 5' domain of the second synthesis primer comprises a second primer site.

16. The method of claim 15, wherein the length of the polynucleotide of interest in the second extension product is from 50 to 10,000 nucleotides.

17. The method of claim 1, wherein polynucleotide of interest is cDNA.

18. The method of claim 1, further comprising repeating said method to obtain the nucleotide sequence of a second desired site in said polynucleotide of interest, and analyzing the sequence obtained in c) and the sequence of the second desired site to obtain linkage information about polymorphisms in said polynucleotide of interest.

* * * * *